(12) United States Patent
Bellew et al.

(10) Patent No.: US 7,814,652 B2
(45) Date of Patent: Oct. 19, 2010

(54) METHOD OF MAKING THROUGH-HOLE VIAS IN A SUBSTRATE

(75) Inventors: Colby Bellew, San Jose, CA (US);
Boyce E. Collins, San Diego, CA (US);
Kelvin Liu, San Diego, CA (US)

(73) Assignee: BioScale, Inc., Cambridge, MA (US)

( * ) Notice: Subject to any disclaimer, the term of this patent is extended or adjusted under 35 U.S.C. 154(b) by 273 days.

(21) Appl. No.: 12/180,169

(22) Filed: Jul. 25, 2008

(65) Prior Publication Data

US 2009/0074951 A1 Mar. 19, 2009

Related U.S. Application Data

(63) Continuation of application No. 10/392,446, filed on Mar. 17, 2003, now abandoned, which is a continuation-in-part of application No. 09/845,521, filed on Apr. 26, 2001, now abandoned.

(60) Provisional application No. 60/233,961, filed on Sep. 20, 2000.

(30) Foreign Application Priority Data

Sep. 20, 2001 (WO) .................... PCT/US01/29487

(51) Int. Cl.
*H01R 43/00* (2006.01)
(52) U.S. Cl. .................... 29/854; 29/830; 29/831; 29/832; 29/712
(58) Field of Classification Search .................. 29/854, 29/830, 831, 832, 712, 709; 422/68.1, 107, 422/108; 435/4, 7.1, 287.2; 427/97.7, 97.2
See application file for complete search history.

(56) References Cited

U.S. PATENT DOCUMENTS

| | | | |
|---|---|---|---|
| 4,426,768 A | 1/1984 | Black et al. | 29/583 |
| 4,874,484 A | 10/1989 | Foell et al. | 204/129.3 |
| 5,157,403 A | 10/1992 | Urkowitz | 342/111 |
| 5,262,021 A | 11/1993 | Lehmann et al. | 204/129.55 |
| 5,424,245 A * | 6/1995 | Gurtler et al. | 438/107 |

(Continued)

FOREIGN PATENT DOCUMENTS

WO 02/25630 A2 3/2002

OTHER PUBLICATIONS

Al-Sarawi, S. F., et al., "A Review of 3-D Packaging Technology." IEEE Transactions on Components, Packaging, and Manufacturing Technology—Part B, vol. 21, No. 1, pp. 2-14, (1998).

(Continued)

*Primary Examiner*—Derris H Banks
*Assistant Examiner*—Tai Nguyen
(74) *Attorney, Agent, or Firm*—Proskauer Rose LLP

(57) ABSTRACT

A sensor assembly for sensors such as microfabricated resonant sensors is disclosed. The disclosed assembly provides improved performance of the sensors by providing a thermally insensitive environment and short pathways for signals to travel to processing components. Further, the assembly provide modular construction for the sensors and housing modules, thereby allowing replacement of the sensors at a lower cost. The assembly includes a sensor module including a sensor formed on a conductive substrate with a cavity formed on one surface. The substrate has conductive vias extending from the cavity to a second surface of the substrate. A housing assembly accommodates the sensor and includes a rigid housing, preferably made from a ceramic. An electronic component, such as an amplifier, is mounted on the rigid housing. The electronic component electrically engages the vias substantially at the second surface of the substrate. The electronic component receive signals from the sensor through the vias. The signals are then processed through an amplifier and a digital signal processor using a modified periodogram.

7 Claims, 7 Drawing Sheets

U.S. PATENT DOCUMENTS

| | | | | |
|---|---|---|---|---|
| 5,445,971 | A | 8/1995 | Rohr | 436/526 |
| 5,490,034 | A | 2/1996 | Zavracky et al. | 361/283.4 |
| 5,511,428 | A | 4/1996 | Goldberg et al. | 73/777 |
| 5,585,068 | A * | 12/1996 | Panetz et al. | 422/64 |
| 5,653,939 | A | 8/1997 | Hollis et al. | 422/50 |
| 5,681,448 | A | 10/1997 | Uchiyama et al. | 205/656 |
| 5,747,116 | A | 5/1998 | Sharan et al. | 427/534 |
| 5,804,741 | A | 9/1998 | Freeman | 73/861.356 |
| 5,870,351 | A | 2/1999 | Ladabaum et al. | 367/163 |
| 5,894,452 | A | 4/1999 | Ladabaum et al. | 367/163 |
| 5,982,709 | A | 11/1999 | Ladabaum et al. | 367/170 |
| 5,983,734 | A * | 11/1999 | Mathur et al. | 73/864.24 |
| 6,033,852 | A | 3/2000 | Andle et al. | 435/6 |
| 6,198,168 | B1 | 3/2001 | Geusic et al. | 257/774 |
| 6,221,769 | B1 | 4/2001 | Dhong et al. | 438/667 |
| 6,222,276 | B1 | 4/2001 | Bertin et al. | 257/778 |
| 6,252,300 | B1 | 6/2001 | Hsuan et al. | 257/686 |
| 6,268,660 | B1 | 7/2001 | Dhong et al. | 257/774 |
| 6,285,063 | B1 | 9/2001 | Splett et al. | 257/415 |
| 6,291,332 | B1 | 9/2001 | Yu et al. | 438/618 |
| 6,297,157 | B1 | 10/2001 | Lopatin et al. | 438/687 |
| 6,391,658 | B1 | 5/2002 | Gates et al. | 438/3 |
| 6,430,109 | B1 | 8/2002 | Khuri-Yakub et al. | 367/181 |
| 6,688,158 | B2 | 2/2004 | Cunningham et al. | 73/24.06 |
| 6,790,775 | B2 | 9/2004 | Fartash | 438/667 |
| 2002/0028519 | A1 | 3/2002 | Yguerabide et al. | 436/518 |
| 2002/0070841 | A1 | 6/2002 | Doppalapudi et al. | 338/5 |
| 2002/0115198 | A1 | 8/2002 | Nerenberg et al. | 435/287.2 |
| 2003/0010745 | A1 | 1/2003 | Field | 216/2 |
| 2003/0119220 | A1 | 6/2003 | Mlcak et al. | 438/52 |
| 2004/0043615 | A1 | 3/2004 | Yamamoto et al. | 438/689 |

OTHER PUBLICATIONS

Anthony, T. R., "Forming electrical interconnections through semiconductor wafers." Journal of Applied Physics, vol. 52, No. 8, pp. 5340-5349 (1981).

Baer, R.L., et al., "Phase Noise Measurements of Flexural Plate Wave Ultrasonic Sensors", 1991 IEEE Ultrasonics Symposium, pp. 321-326, (1991).

Bean, Kenneth E., "Anisotropic Etching of Silicon." IEEE Transactions on Electron Devices, vol. 25, No. 10 pp. 1185-1193, (1978).

Belov, Larissa., et al., "Immunophenotyping of Leukemias Using a Cluster of Differentiation Antibody Microarray." Cancer Research, vol. 61, pp. 4483-4489, (2001).

Britton, C. L. et al., "Multiple-input microcantilever sensors." Ultramicroscopy, vol. 82, pp. 17-21, (2000).

Carstensen, J., et al., "Pore formation mechanisms for the Si-HF system." Materials Science and Engineering, B69-70, pp. 23-28, (2000).

Chow, E. M., et al., "Integration of through-wafer interconnects with a two-dimensional cantilever array." Sensors and Actuators, vol. 83, pp. 118-123, (2000).

Costello, B.J., et al., "A Flexural-Plate-Wave Microbial Sensor", IEEE, 0-7803-0456-X/92, pp. 69-72.

Cunningham, B. et al., "Design, fabrication and vapor characterization of a microfabricated flexural plate resonator sensor and application to integrated sensor arrays," Sensors and Actuators B, vol. 73, pp. 112-123 (2001).

Das, P. "A Pressure Sensing Acoustic Surface Wave Resonator", Ultrasonics Symposium Proceedings, IEEE, pp. 306-308, (1976).

Dougherty, G. M., et al.; "Processing and Morphology of Permeable Polycrystalline Silicon Thin Films." Department of Materials Science and Engineering and Department of Mechanical Engineering, University of California—Berkeley—J. Mater. Res., vol. 17, No. 9, pp. 2235-2242, (2002).

Gianchandani, et al., "A Bulk Silicon Dissolved Wafer Process for Microelectromechanical Devices", Journal of Microelectromechanical Systems, vol. 1, No. 2, pp. 77-85, (1992).

Giesler, T. et al., "Electrostatically excited and capacitively detected flexural plate waves on thin silicon nitride membranes with chemical sensor applications," Sensors and Actuators B, vol. 18-19, pp. 103-106, (1994).

Grate, J.W., et al., "Acoustic Wave Microsensors—Part I" Analytical Chemistry, vol. 65, No. 21, pp. 940A-948A, (1993).

Grate, J.W., et al., "Acoustic Wave Microsensors—Part II" Analytical Chemistry, vol. 65, No. 22, pp. 987A-996A, (1993).

Grate, J.W., et al., "Flexural Plate Wave Devices for Chemical Analysis", Analytical Chemistry, vol. 63, pp. 1552-1561, (1991).

Grate, J.W., et al., "Smart Sensor System for Trace Organophosphorus and Organosulfur Vapor Detection Employing a Temperature-Controlled Array of Surface Acoustic Wave Sensors, Automated Sample Preconcentration, and Pattern Recognition", Analytical Chemistry, vol. 65, No. 14, pp. 1868-1881, (1993).

Han, C. et al., "Micromachined Piezoelectric Ultrasonic Transducers Based on Parylene Diaphragm in Silicon Substrate," 2000 IEEE Ultrasonics Symposium, vol. 1, 22-25, pp. 919-923, (2000).

Hart, Darren J., et al., "The salt dependence of DNA recognition by $Nf_{-\kappa}B$ p50: a detailed kinetic analysis of the effects on affinity and specificity." Nucleic Acids Research, vol. 27, No. 4, pp. 1063-1069, (1999).

Houseman, Benjamin T., et al., "Peptide chips for the quantitative evaluation of protein kinase activity." Nature Biotechnology, vol. 20, pp. 270-274, (2002).

Huston, James S. et al. "Protein Engineering of Antibody Binding Sites: Recovery of Specific Activity in an Anti-Digoxin Single-Chain Fv Analogue Produced in *Escherichia coli*." Proceedings of the National Academy of Sciences of the United States of America, vol. 85, No. 16, pp. 5879-5883, (1988).

Jaafar, Maha A. S. and Denton, D. D., "A Plated Through-Hole Interconnect Technology in Silicon." Journal of Electrochemical Society, vol. 144, No. 7, pp. 2490-2495, (1997).

Jain, M.K., et al., "Measurement of Temperature and Liquid Viscosity Using Wireless Magneto-Acoustic/MagnetoOptical Sensors," IEEE Transactions on Magnetics, vol. 37, No. 4, pp. 2767-2769, (2001).

Kim, S. et al., "The Fabrication of Thin-Film Bulk Acoustic Wave Resonators Employing a ZNO/Si Composite Diaphragm Structure Using Porous Silicon Layer Etching," IEEE Electron Device Letters, vol. 20, pp. 113-115, (1999).

Kleimann, P. et al., "Formation of wide and deep pores in silicon by electrochemical etching." Materials Science and Engineering B69-70, pp. 29-33, (2000).

I. Ladabaum et al., "Surface Micromachined Capacitive Ultrasonic Transducers," IEEE Transactions on Ultrasonics, Ferroelectrics, and Frequency Control, vol. 45, No. 3, pp. 678-690, (1998).

Lal, Sean. P., "Antibody arrays: an embryonic but rapidly growing technology." DDT, vol. 7, No. 18 (Suppl.), pp. S143-S149, (2002).

Lebouitz, Kyle S. et al., "Permeable Polysilicon Etch-Access Windows for Microshell Fabrication." Transducers'95 Eurosensors IX, the 8th International Conference on Solid State Sensors and Actuators and Eurosensors IX, Digest of Technical Papers, Jun. 25-29, 1995, Stockholm, Sweden, vol. 1, Sessions Al-PD6, Papers 1-231, p. 224-227.

Lebouitz, Kyle S. et al., "Vaccum Encapsulation of Resonant Devices Using Permeable Polysilicon." IEEE International MEMS '99 Conference, Twelfth IEEE International Conference on Micro Electro Mechanical Systems, IEEE Catalog Number: 99CH36291C, pp. 470-475, (1999).

Lee, H., et al., "Silicon Bulk Micromachined High Q Film Bulk Acoustic Resonator Devices with Mo/AlN/Mo Structures," Integrated Ferroelectrics, vol. 69, pp. 323-332, (2005).

Lehmann, V. And Föll, H., "Formation Mechanism and Properties of Electrochemically Etched Trenches in n-Type Silicon." Journal of the Electrochemical Society, vol. 137, No. 2, pp. 653-659, (1990).

Lehmann, V., "Porous Silicon—A New Material for MEMS." *IEEE.*, pp. 1-6, (1996).

Lieb, Jason. D., et al., "Promoter-specific binding of rap1 revealed by genome-wide maps of protein-DNA association." Nature Genetics, Advanced Online Publication, http://genetics.nature.com, pp. 1-8, (2001).

Lukosz, W., "Principles and sensitivities of integrated optical and surface plasmon sensors for direct affinity sensing and immunosensing." Biosensors & Bioelectronics, vol. 6, pp. 215-225, (1991).

Pyun, J.C., et al., "Development of a biosensor for E. coli based on a flexural plate wave (FPW) transducer." Bionsensors & Bioelectronics, vol. 13, pp. 839-845, (1998).

Reeder, T., et al., "Surface-Acoustic-Wave Pressure and Temperature Sensors", Proceedings of the IEEE, vol. 64, pp. 754-756, (1976).

Robinson, W. H., et al., "Autoantigen microarrays for multiplex characterization of autoantibody responses." Nature Medicine, vol. 8, No. 3, pp. 295-301, (2002).

Rosén, Daniel., et al., "Membrane covered electrically isolated through-wafer via holes." Journal of Micromechanics and Microengineering, vol. 11, pp. 344-347, (2001).

Schlessinger, Joseph, "A solid base for assaying protein kinase activity." Nature Biotechnology, vol. 20, pp. 232-233, (2002).

Schweitzer, Barry., et al., "Immunoassays with rolling circle DNA amplification: a versatile platform for ultrasensitive antigen detection." PNAS, vol. 97, No. 18, pp. 10113-10119, (2002).

Seed, B., et al., "Molecular cloning of the CD2 antigen, the T-cell erythrocyte receptor, by a rapid immunoselection procedure." Proc. Natl. Acad. Sci., vol. 84, pp. 3365-3369, (1987).

Soh, Hyongsok T., et al., "Ultra-Low Resistance, Through-Wafer Via (TWV) Technology and Its Applications in Three dimensional Structures on Silicon." Japanese Journal of Applied Physics, vol. 38, No. 4B, pp. 2393-2396, (1999).

Tabata, Osamu., et al., "Anisotropic etching of silicon in TMAH solutions." Sensors and Actuators, vol. A34, pp. 51-57, (1992).

Takizawa, Takashi., et al., "Conductive Interconnections Through Thick Silicon Substrates for 3D Packaging." IEEE pp. 388-391, (2002).

Vanhamme, L., et al., "Biomedical Magnetic Resonance Spectroscopic Quantitation: a Review of Modern time-domain Analysis Methods.", pp. 685-693.

Waters, W. R., et al., "Five-Color Flow Cytometric Analysis of Swine Lymphocytes for Detection of Proliferation, Apoptosis, Viability, and Phenotype." Cytometry, vol. 48, pp. 146-152, (2002).

Wenzel, S.W., et al., "Analytic comparison of the sensitivities of bulk-wave, surface-wave, and flexural plate-wave ultrasonic gravimetric sensors", Appl. Phys. Lett., vol. 54, No. 20, pp. 1976-1978, (1989).

Westin, Lorelei, et al., "Anchored multiplex amplification on a microelectronic chip array." Nature Biotechnology, Vol. 18, pp. 199-204, (2000).

White, R.M., et al., Plate-Mode Ultrasonic Oscillator Sensors, IEEE Transactions on Ultrasonics, Ferroelectrics, and Frequency Control, vol. 34, pp. 162-171, (1987).

Wrobel, L. K., et al., "Contractility of Single Human Dermal Myofibroblasts and Fibroblasts." Cell Motility and the Cytoskeleton, vol. 52, pp. 82-90, (2002).

Yu, Y., et al., "High Quality Silicon-Based AlN Thin Films for MEMS Application," Integrated Ferroelectrics, vol. 69, pp. 367-374, (2005).

* cited by examiner

METHOD OF MAKING THROUGH-HOLE VIAS IN A SUBSTRATE

This application is a continuation of U.S. patent application Ser. No. 10/392,446, entitled SUBSTRATES HAVING THROUGH-HOLE VIAS AND METHOD OF MAKING SAME, filed Mar. 17, 2003; which is a continuation in part of U.S. patent application Ser. No. 09/845,521, entitled MICROFABRICATED ULTRASOUND ARRAY FOR USE AS RESONANT SENSORS, filed Apr. 26, 2001; which claims priority to U.S. Provisional Patent Application No. 60/233,961, filed Sep. 20, 2000; and of International Application No. PCT/US01/29487, entitled MICROFABRICATED ULTRASOUND ARRAY FOR USE AS RESONANT SENSORS, filed Sep. 20, 2001, each of which is hereby incorporated by reference in its entirety, including all tables, figures and claims.

FIELD OF THE INVENTION

The present invention relates to sensors for monitoring a change in force as applied to a surface membrane or a change in the surface properties of the sensor membrane. More particularly, the invention relates to a microfabricated mechanical resonant sensor and a sensor assembly.

BACKGROUND

The following description is provided to assist the understanding of the reader. None of the information provided or references cited is admitted to be prior art to the present invention.

Technological advances in combinatorial chemistry, genomics. and proteomics have fostered an increased need for rapid high throughput (HTP) screening methods able to monitor and/or detect the reaction between one or more target species and binding partners or potential binding partners of such targets. Various systems have been, and are being, explored to detect analytes. Systems such as affinity chemical sensing, arrayed sensors, and acoustic sensors are being investigated for their respective usefulness in detecting analytes in clinical and non-clinical settings.

Affinity Chemical Sensing

Affinity chemical sensing systems attempt to detect interactions between a target analyte and an appropriate binding partner. Such systems generally rely on the production or use of a detectable signal. Affinity chemical sensing systems employ binding partners which can be discrete molecular species to which the target analyte specifically binds, or a phase, such as an organic polymer, into which the target partitions. Covalently attached labels such as, fluorescent, electrochemical, radioactive, or mass based-probes are typically employed in such systems. Methods for determining the presence analytes by using systems that detect the inherent optical, electrochemical, or physical properties of a target species or changes in the properties of the layer containing the binding partner to which a target species binds, have been employed to detect and/or monitor un-labeled analytes.

Charych, et al., U.S. Pat. No. 6,022,748, filed Aug. 29, 1997, describe an example of a sensor employing an optically active sensor coating that changes color upon binding of the target. Further example of affinity sensing methods are described by W. Lukosz, "Principles and sensitivities of integrated optical and surface plasmon sensors for direct affinity sensing and immunosensing", Biosensors & Bioelectronics 6, 1991, pp. 215-225. Utilization of surface plasmon resonance in sensing applications is also described by Hanning in U.S. Pat. No. 5,641,640, filed Dec. 29, 1994. A Chemically Selective Field Effect Transistor (CHEMFET) that determines target binding by monitoring a signal change on the sensor surface in response to target binding to the said surface, is described by Shimada in U.S. Pat. No. 4,218,298, filed Nov. 3, 1978. Ribi et al., in U.S. Pat. Nos. 5,427,915 and 5,491,097, filed Aug. 9, 1993 and Feb. 28, 1994 respectively, describe affinity-based microfabricated sensors in which a measurable change in conductivity of a bio-electric sensor layer is used to determine binding of a target species.

Arrayed Sensors

Arrayed sensors have multiple individually addressable sites on the device surface which are modified to contain binding partners for a target molecule to be detected. An example of such a detection system can be found in U.S. Pat. No. 6,197,503, filed Nov. 26, 1997 by Vo-Dinh et al. The patent describes a device employing multiple optical sensing elements and microelectronics on a single integrated chip combined with one or more nucleic acid-based bioreceptors designed to detect optically labeled, sequence specific genetic constituents in complex samples.

Other examples of arrayed sensors include: Pinkel et al., U.S. Pat. No. 6,146,593 filed Jul. 24, 1997, describe a method for fabricating biosensors using functionalized optical fibers to create a high density array of uniquely addressable biological binding partners; Fodor et al., U.S. Pat. No. 6,124,102 filed Apr. 21, 1998 describe an optical sensor array having a planar surface derivatized with ligands of an optically active target species immobilized at known locations such that each location comprises a "pixel" of an optical read out device. These and similar devices can be successful for arrayed detection and therefore useful for parallel screening of multiple interactions where the analyte is either labeled or inherently optically, electrically, or specifically chemically active.

Acoustic Sensors

Another-field of technology having combine arrayed sensors is that of sensors based on bulk or microfabricated resonant devices. Such sensors have been demonstrated in systems used to determine 3-dimensional acceleration, speed, and position, as transducers for monitoring environmental conditions such as pressure, fluid flow, temperature, and as gravimetrically sensitive elements in chemical affinity sensors.

Acoustic sensors for chemical sensing have been demonstrated in low-density arrays in for example Ballato U.S. Pat. No. 4,596,697 filed Sep. 4, 1984 which describes surface acoustic wave (SAW) devices. Arrays of cantilever sensors for gas phase sensing of multiple analytes are described by Lang et al (Lang, H. P.; Baller, M. K.; Berger, R.; Gerber, Ch.; Gimzewski, J K.; Battiston, F M; Fornano, P.; Ramseyer, J. P.; Meyer, E.; Guntherodt, H. J.; IBM Research Report, RZ 3068 (#93114), Oct. 19, 1998), and Britton et al (Britton, C. L.; Jones, R. L.; Oden, P. I.; Hu, Z.; Warmack, R. J.; Smith, S. F.; Bryan, W. L.; Rochelle, J. M.; Ultramicroscopy, 82, 2000, p. 17-21).

SUMMARY OF THE INVENTION

The invention described herein relates to sensors and sensor assemblies that can be used for various applications. The disclosed embodiments provide a sensor assembly that is tolerant to changes in environmental or system temperature changes. Further, the disclosed embodiments provide a sensor package that provides a modular construction, leading to a significant reduction in cost. Finally, the invention provides for transmission and processing of signals from the sensor to electronic components, such as amplifiers, for more accurate and sensitive analysis. Current evanescent sensors known in the art require interactions to be very close to the surface. Acoustic sensors do not perform well in aqueous environments. Electronic sensors remain relatively insensitive. The current patent discloses methods and compositions that provide sensors, and preferably arrays of sensors, that perform well in water, have a good electrical interface, minimize interference, have a rapid and accurate signal processing scheme to allow sub Hz resolution of frequency shifts. The sensors of the present invention are particularly advantageous in biologic applications, where aqueous environments are the norm.

The sensor in the package may be a microfabricated resonant sensors for monitoring a change in surface properties of a sensor membrane that can be used individually or as an interconnected, yet electrically isolated, grouping in microarrays. The change in surface properties results from a binding event that changes the physical characteristics of the membrane surface, such as surface mass, viscous coupling, membrane stiffness, and the like. The sensors can also be used to determine a change in force on the surface of a sensor membrane, such as results from a binding event or application of pressure. A sensor can be part of an array of sensors which can be fabricated to high density. The sensors and the sensor assembly of the present invention may have many applications and may provide improved performance over existing devices.

The term "sensor" as used herein relates to an apparatus or device that can respond to an external stimulus such as, a change in mass on a surface, pressure, force, or a particular motion, where the apparatus can transmit a resulting signal to be measured and/or detected.

The term "binding event" refers to an interaction or association between a minimum of two molecular structures, such as an analyte and a binding partner. The interaction may occur when the two molecular structures are in direct or indirect physical contact. Examples of binding events of interest in the present context include, but are not limited to, ligand/receptor, antigen/antibody, enzyme/substrate, DNA/DNA, DNA/RNA, RNA/RNA, nucleic acid mismatches, complementary nucleic acids, nucleic acid/proteins, and the like.

The term "analyte" or "target" refers to any molecule being detected by the sensor. The analyte (or target) is detected by immobilizing one or more binding partners (or "probes") or presumed binding partners specific for the analyte or target to a sensor membrane. Thus, when it is desired to use the sensor to determine if a gas or solution contains an analyte, the surface of the sensor membrane that is to contact the gas or solution is immobilized with a binding partner for that analyte. Analyte and its binding partner represent a binding pair of molecules, which interact with each other through any of a variety of molecular forces including, for example, ionic, covalent, hydrophobic, van der waals, and hydrogen bonding, so that the pair have the property of binding specifically to each other. Specific binding means that the binding pair exhibit binding with each other under conditions where they do not bind to another molecule. Examples of types of specific binding pairs are antigen-antibody, biotin-avidin, hormone-receptor, receptor-ligand, enzyme-substrate, IgG-protein A, and the like.

Analytes or binding partners may be naturally occurring or synthetically prepared. A "natural analyte" is an analyte which occurs in nature and specifically binds to a particular site(s) on a particular binding partner such as a protein. Examples by way of illustration and not limitation include a receptor and a ligand specific for the receptor (e.g., an agonist or antagonist), an enzyme and an inhibitor, substrate or cofactor; and an antibody and an antigen.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. An antibody can be specific for a particular antigen. The antibody or its antigen can be either an analyte or a binding partner.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to VH-CH1 by a disulfide bond. The $F(ab)'_2$ may be reduced under mild conditions to break the disulfide linkage in the hinge region thereby converting the $(Fab')_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv") polypeptide is a covalently linked VH::VL heterodimer which may be expressed from a nucleic acid including VH- and VL-encoding sequences either joined directly or joined by a peptide-encoding linker. Huston, et al. (1988) Proc. Nat. Acad. Sci. USA, 85:5879-5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complimentarily determining regions" or "CDRs" and are characterized, for example by Kabat et al. Sequences of proteins of immunological interest, 4th ed. U.S. Dept. Health and Human Services, Public Health Services, Bethesda, Md. (1987). An epitope is that portion of an antigen that interacts with an antibody.

"Sample" refers to essentially any source from which an analyte can be obtained. A sample may be acquired from essentially any organism, including animals and plants, as well as cell cultures, recombinant cells, cell components and can also be acquired from environmental sources. Samples can be from a biological tissue, fluid or specimen and may be obtained from a diseased or healthy organism. Samples may include, but are not limited to, sputum, amniotic fluid, blood, blood cells (e.g., white cells), urine, semen, peritoneal fluid, pleural fluid, tissue. or fine needle biopsy samples, and tissue homogenates. Samples may also include sections of tissues such as frozen sections taken for histological purposes. Typically, samples are taken from a human. However, samples can be obtained from other mammals also, including by way of example and not limitation, dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used. A sample also my be artificially prepared such as a control sample that contains a known amount of an analyte.

Biological samples can be derived from patients using well known techniques such as venipuncture, lumbar puncture, fluid sample such as saliva or urine, or tissue biopsy and the like. Biological samples also include exhaled air samples as taken with a breathalyzer or from a cough or sneeze. A biological sample may be obtained from a cell or blood bank where tissue and/or blood are stored, or from an in vitro source, such as a culture of cells. Techniques for establishing a culture of cells for use as a source for biological materials are well known to those of skill in the art. Freshney, Culture of Animal Cells, a Manual of Basic Technique, Third Edition, Wiley-Liss, N.Y. (1994) provides a general introduction to cell culture.

As used herein "microfabricated" refers to the procedures and/or methods, such as bulk and surface micromachining, used to etch, deposit, pattern, dope, form and/or fabricate structures using substrates such as silicon and the like. Microfabrication procedures are known in the art and have been used to prepare microsystems such as computer processor chips, acoustic sensors, micro-circuits and other devices requiring micron and nanomolecular scale portions used in fields such as microengineering.

In one aspect, the present invention provides a micromechanical sensor assembly for detecting, for example, a change in force at a membrane surface or a change in the surface properties of the sensor membrane. The sensor assembly of the invention comprises a sensor module including a sensor formed on a substrate. The substrate has conductive vias extending to a second surface of the substrate. The sensor assembly further comprises a housing assembly adapted to accommodate the sensor The housing assembly includes a rigid housing and is adapted to accommodate an electronic component mounted on the rigid housing. The electronic component is adapted to electrically engage the vias substantially at the second surface of the substrate. The electronic component is further adapted to receive signals from the sensor through the vias.

As used herein, the term "module" refers to a portion of an assembly that may include a set of related components. A module may be interchangeable with like modules.

The term "substrate" is used herein to refer to the starting material from which the sensor of the invention is fabricated. The substrate can comprise single crystal silicon, glass, gallium arsinide, silicon insulator, silicon-on-sapphire, and indium phosphate, and the like. Also, combinations of these materials can be used. Preferably, the substrate has a high electrical resistance, such as a P or N-type silicon wafer rated up to 15,0000' $\Omega \cdot cm$. In a particular embodiment, the substrate comprises a silicon wafer, double side polished, P or N-type substrate having a resistance between 5 and 15,0000' $\Omega \cdot cm$. More preferably, the substrate is a double side polished, silicon wafer, P or N-type having a resistance of roughly 10,0000 $\Omega \cdot cm$. The substrate of the sensor can comprises one or more dopants, for example boron and/or phosphorus, to be patterned as one or more electrodes, and any vents, passages or holes within the cavity can extend through the substrate.

The term "via" is used herein to refer to a channel or a set of channels directed through a substrate. A via may be conductive or non-conductive. Further, a via may be either filled with a material or may be hollow. Vias may extend in any direction. Preferably, vias described in this invention run substantially perpendicular to the planar surfaces of the substrate.

As used herein, the term "housing" refers to an enclosure or support structure. Housing may be used to isolate components from the environment or to provide a stable environment for the components. Further, housing may simply provide abase for the components.

The term "rigid" is used herein to characterize the resistive tendency of a structure against vibrations, fluidity or other disruptive movements. In one regard, rigid refers to tolerance to thermal variations through low coefficients of thermal expansion.

The term "electrically engage" refers to an arrangement for allowing electrical communication. Components are generally electrically engaged through physical interconnection.

In a preferred embodiment, the sensor comprises a membrane on the first surface enclosing the cavity and a second electrode spaced apart from the first electrode. The membrane includes a first electrode. The membrane may be adapted to produce a membrane response when electrically activated.

The membrane of the sensor can be polygonal or elliptical. In a preferred embodiment, the membrane is rectangular having sides of 5 to 10 microns in length. In another preferred embodiment, the membrane is circular having a radius between 2 and 100 microns. The membrane covers a cavity in the substrate in a manner that prevents a fluid from entering the cavity. Preferably, the membrane is up to 0.5 microns thick. More preferably, the membrane is at least 0.05 microns and up to 0.5 microns thick.

The cavity is preferably 0.1 to 2 microns deep and is sealed with the membrane. Preferably, the cavity comprises one or more walls that are 0.1 to 2 microns in height. More preferably, the cavity walls are 0.3 to 1 micron in height, creating a cavity that is approximately 0.3 to 1 micron deep. The height of the cavity is indicative of the distance between the electrodes of the sensor forming a capacitor.

The membrane or membrane layer of the sensor can be fabricated from an electrically conductive material, such as doped single crystal silicon, doped polysilicon, metal or any composite thereof, and can serve as a connection to ground. In alternative embodiments, the membrane can be fabricated out of non-conductive materials such as silicon nitride, silicon dioxide, phosphosilicate glass, borophosphosilicate glass. In this case, the membrane is not an electrode but can have an electrode fabricated within, on, above or below the surface. As discussed herein, the membrane covers roughly the entire opening of the cavity in a substantially sealed manner. The membrane of the sensor can also serve to conduct an electrical signal. In another embodiment the membrane layer can be fabricated to contain one or more secondary structures that can conduct a current of electricity such as piezoelectric or piezoresistive materials. In selecting a material to serve as a membrane for the invention sensor, certain mechanical characteristics such as Young's Modulus, which refers to the stiffness of the membrane, the density, the intrinsic stress, and internal damping are considered. In a preferred embodiment of the present invention the membrane is prepared or fabricated in a manner that allows the membrane to vibrate and/or resonate. The membrane can also be fabricated to either serve as an electrode for conducting electricity, or as a connection to ground. The membrane can serve as part of a capacitive or electrostatic pair. Within this embodiment, the membrane and the other electrode of the pair are separated by the space of the cavity and/or materials within the cavity, and act as a capacitor like structure.

As used herein the term "membrane response" relates to the vibration or resonance of the membrane layer that is extended over, or placed on, and roughly covers, in a sealed liquid impermeable, manner a cavity of the invention sensor. Upon the introduction of a current or formation of an electrostatic potential, the membrane of the invention can move, vibrate or oscillate in a manner that can be measured, for example, acoustically, electronically by electromechanical transduction such as by electrostatics/capacitance, piezoresistance or piezoelectricity, or optically by interferometry, such as laser-Doppler vibrometery. The extent of vibration or oscillation of the membrane depends, for example, on the physical properties of the membrane and its relation to another electrode in the cavity or the effect of mass or force on the membrane surface.

In a preferred embodiment, the rigid housing is formed of a ceramic. In a more preferred embodiment, the rigid housing is formed of a low-temperature co-fired ceramic (LTCC). In a further preferred embodiment, the housing is formed in layers of LTCC. In a still further preferred embodiment, wire leads may be provided to extend from the electronic component and through the layer of LTCC.

The electronic component may include stud contacts for electrically engaging the vias. "Stud contacts" refers to protrusions made of conductive material that are adapted to electrically connect two components. The stud contacts may be shaped to provide electrical contact with a variety of components or may be customized to contact a specific component. In a still further embodiment, the stud contacts are gold studs. These may interface with conductive polymer sheets such as Z-tape or Z-foam and allow reversible interconnection with electronics below or may be permanently bonded to the electrical interface below.

The sensor module may further include a reservoir formed on the first surface of the sensor. The reservoir is adapted to retain a sample solution therein. The sample solution may be a liquid or a gel containing a volume of sample to be tested, for example, for the presence or absence of an analyte.

In one preferred embodiment, the sensor module includes a non-conductive frame for the sensor. The nonconductive frame at least partially forms the reservoir and is adapted to support the sensor on the housing assembly. The nonconductive frame may be formed of a ceramic. In a preferred embodiment, the frame is formed from an alumina card, which may be provided with holes or cavities formed therein to accommodate components or the reservoir.

The cavity in the substrate may be substantially evacuated and sealed. Evacuating the cavity may be performed in any number of known ways. The level of evacuation may be determined according to the desired sensitivity of the sensor, for example.

The sensor assembly may also include sealable vent channels extending from the cavity to the second surface for venting the cavity. The sealable vent channels may be used to evacuate the cavity, or may be used to, occasionally vent the cavity to the atmosphere to normalize or calibrate the operation of the sensor.

The vias in the substrate may include coaxial channels that may be formed in a single hollowed channel and may be either insulated from each other or may be adjacent to each other. In a preferred embodiment, the coaxial channels include an outer conductive channel and an inner conductive channel The outer channel may be used for electrically shielding the inner channel.

"Coaxial channels" refers to an arrangement wherein two or more channels have a substantially similar longitudinal axis. In this arrangement, the two channels may appear as, for example, concentric circles in a cross-sectional view. Of course, cross-sectional configurations other than circles may be used as well.

The electronic component may be one of many components, such as an amplifier. An amplifier may be used to boost a low-strength signal from the sensor so that it may be further processed and/or analyzed or may be used to convert the high impedance of a small capacitive sensor to a lower impedance output to improve signal to noise ratios.

The sensor assembly may also be provided with a fluidics module for flowing a sample fluid to and from a sensor region of the sensor. A sensor region may be a surface area or a volume near, for example, a membrane of the sensor. The fluidics module may include a base supported on the rigid housing. The base should generally be formed from a material having a low coefficient of thermal expansion, preferably a ceramic and, more preferably, alumina.

The sensor module and the housing assembly may be modular and interchangeable with other respective sensor modules and housing assemblies. In this regard, a sensor module may be made discardable after a certain number of uses without the need to replace the entire assembly, which may include expensive electronics, for example.

In another aspect of the invention, a sensor element comprises a substrate having at least one cavity formed on a first surface and a membrane on the first surface. The membrane encloses the cavity and includes a first electrode. The sensor element further includes a second electrode spaced apart from the first electrode. At least one via extends to a second surface of the substrate, the second surface being opposite of the first surface. The via includes at least two coaxial channels.

In a preferred embodiment, the coaxial channels include an outer conductive channel and an inner conductive channel. Alternatively, the coaxial channels may include an outer conductive channel and an inner fluid channel. The inner fluid channel may be used to vent the cavity to atmosphere.

The coaxial channels may be separated by an insulating layer. As used herein, "insulating layer" refers to a layer of non-conductive material that may be deposited or grown on a surface. Such non-conductive materials may include a variety of materials such as oxides.

The cavity in the substrate may be substantially evacuated. "Substantially evacuated," as used herein, refers to a low-pressure environment, preferably having a pressure of less than 1 T.

In another aspect, the invention provides a method of forming a substrate for a sensor element. According to the method, a via from a first surface of the substrate to a second surface of the substrate is formed. This may include electrochemically etching the substrate. Various methods of electrochemical etching are known to those skilled in the art. The walls of the via are then coated with a first insulating layer. This may be accomplished by growing a conformal insulating layer. The conformal insulation is grown onto a surface to form a thin layer. A first conductive layer is formed over the first insulating layer. The first conductive layer extends substantially from the first surface to the second surface, and the conductive layer has a hollow, central channel therethrough. The first conductive layer may be formed by filling a central region through the insulating layer with a conductive material, and etching the conductive material to form the hollow central channel therethrough.

In a preferred embodiment, the method further includes coating the walls of the hollow, central channel with a second insulating layer, thereby forming a hollow insulated channel through the first conductive layer. In this regard, the hollow insulated channel is insulated from the first conductive layer. The insulated channel may be filled with a conductive material, thereby forming a second conductive channel through the via. Thus, two or more coaxial conductive channels may be formed in the via.

In another aspect, the invention provides a method of processing sensor signals. According to the method, signals from a sensor are digitized, and the digital signals are processed using a periodogram. The signals are responsive to a resonator that may drive a sensor membrane, for example. The periodogram is provided with a time-weighted component adapted to weigh signal components according to a signal-to-noise ratio of said signal components.

A periodogram is a function for processing digital signals. The periodogram may be used to normalize the power spectrum for a signal or signals in order to identify the signal in the presence of noise by estimating the power spectral density. The power spectral density is the distribution of power over a range of the frequency spectrum. Thus, a periodogram may output a frequency having a maximum power density, thereby identifying the signal frequency from the noise.

In a preferred embodiment, the time-weighted component is a time-decaying component. In this regard, because the signal is decaying with time, the ratio of signal to noise is also decaying. Thus, a time-decaying component used for weighting the original samples will bias the output to the signal samplings with a higher (better) signal-to-noise ratio.

In a further preferred embodiment, the periodogram is defined by:

$$\frac{1}{N}\left|\sum_{n=0}^{N-1} x(n)e^{-\alpha nT}e^{-i\omega T}\right|^2;$$

where $x(n)$ is an impulse response of said resonator, is angular frequency, $T$ is a selected sample period, and $\alpha$ is an empirically determined constant. In this regard, the angular frequency may range from 0 to $2\pi$ for the entire spectrum. By applying a typical optimization technique (e.g., golden-ratio optimization), one can apply the above formula at a small number of different frequencies and identify the resonance frequency to approximately within 1 Hz. Empirically, it has been demonstrated that only the periodogram at fewer than 30 frequencies need to be calculated to achieve the desired frequency resolution. With tighter manufacturing control, the number of frequencies where periodogram computation is required may be further reduced, and the computational load of the system can, therefore, also be reduced.

In another aspect, the present invention relates to methods for use of resonant sensors to detect one or more binding events at or near to the resonant membrane, and devices for performing such methods. As described in detail herein, the frequency of membrane resonance in such sensors is sensitive to the mass attached to the membrane, as well as to changes in mass in a geometric region above the sensor. While the exact shape of this region (e.g., spherical or parabolic) may vary, for the sake of simplicity, this shape may be approximated by a sphere having a diameter equal to that of the diameter of the membrane of the sensor. The area queried extends in the z axis dimension perpendicular to the plane of the membrane, and the sensor may be employed to sense differences in density within this region. As used herein, this concept of density sensing is referred to as detection of an event "at or near" the resonant membrane surface.

While a device comprising a resonant sensor may comprise a single sensor, in preferred embodiments the resonant sensor is formed into a resonant sensor array comprising a plurality of discretely addressable resonant sensors in a single physical device. Resonant sensor(s) can be arranged in an array from as few as a handful of sensor sites to as many as 500,000 individual sensors/cm$^2$ High density arrays can comprises between 256 to 150,000 individual sensors/cm$^2$ and more preferably between 5,000 to 100,000 sensors/cm$^2$. Each sensor in the array can be configured and arranged to detect the same binding event (e.g., each sensor may comprise one or more binding partners for the same analyte of interest). However, in some embodiments, one or more individual sensors within an array can be configured and arranged to detect different binding events (e.g., one or more sensors in an array may comprise one or more binding partners for a first analyte of interest, while one or more different sensors in the array comprise one or more binding partners for a second analyte of interest). Preferably, an array comprises discretely addressable resonant sensors for the detection of 2, 3, 4, 5, 10, 20, 50, 100, 200, 500, 1000, 2000, 5000, 10000, 50000, 100000, 200000, 500000, or more different analytes.

It is preferred that individual sensors sites are arranged in the array in a manner that allows for electrical isolation of each sensor. In some embodiments, the individual sensor sites can be individually addressed. In other embodiments, multiple sensor sites may be linked so that they can be actuated and detected simultaneously.

By the term "addressable" when describing the electrical potential of the sensor, membrane, electrode or an array, is meant that the described layer, sensor, substrate and/or membrane can accept an electron, have an electric potential or voltage assignment. The electric potential can be the assignment of having a ground voltage, such as for example the membrane can be held at ground voltage when a sensor operates using an AC, alternating current, power source, or the assignment can be a lower or higher electric potential within the membrane in reference to an opposing electrode if using a DC, direct current, electrode power source. The term "addressable" when used to describe a sensor when placed in an array, combines the concept of assigning an electric potential or voltage and relates to each sensor being capable of being given a specific locator and/or identifier, allowing a particular sensor in an array to be separately identifiable from surrounding sensors when used in methods such as high through put screening.

Resonant sensors may also be formed into arrays having various physical dimensions and forms. For example, the sensors may be formed into an array that is substantially circular, elliptical, square, rectangular, etc. Preferably, the sensors are formed into an array having a radius (if a circle) or axis (if an ellipse, square, or rectangle) that is between 200 μm and 200 mm, more preferably between 500 μm and 100 mm, and most preferably between 1 mm and 50 mm.

In various embodiments, the resonant sensor(s) employed in this aspect are those disclosed in U.S. patent application Ser. No. 09/845,521, entitled MICROFABRICATED ULTRASOUND ARRAY FOR USE AS RESONANT SENSORS, filed Apr. 26, 2001; and International Publication No. WO 02/25630, entitled MICROFABRICATED ULTRASOUND ARRAY FOR USE AS RESONANT SENSORS, published on Mar. 28, 2002, each of which is hereby incorporated in its entirety, including all tables, figures, and claims. In particularly preferred embodiments, the resonant sensor(s) employed in this aspect are those described in detail herein.

In preferred embodiments, resonant sensors or resonant sensor arrays are used to detect the binding of a cell or vesicle at or near the resonant membrane surface. Cells, fixed or living, typically have diameters of 1-2 μm (bacteria), 7-10 μm (erythrocytes and white blood cells) and 20-40 μm (tissue culture cells). Because they contain large amounts of DNA (density 1.5 g/mL), RNA (1.7 g/mL) and protein (1.3 g/mL), intact cells have a density greater than that of water: 1.09 $g/cm^3$ for erythrocytes and 1.07 $g/cm^3$ for white blood cells (with water having a density of 1.0 $g/cm^3$). Thus, cells passing near the sensor will be detected as perturbations in density, causing the membrane to resonate at a lower frequency, without the need for any additional label.

Resonant sensors or resonant sensor arrays may be used for purposes of "cell panning." As used herein, the term "cell panning" refers to the binding of a cell to a surface due to specific binding of the cell to a binding partner for a cell surface epitope that is immobilized on the surface. The array format described herein permits cell panning to be performed in parallel; that is, binding partners for one or more different cell surface molecules (e.g., epitopes, receptors, etc.) may be bound to different sensors in the array, and binding may be determined at each sensor in the array by detecting a change in resonant frequency at a given sensor.

In various embodiments, array-based cellular panning may be used to determine the phenotype of cells in a cell population. For example, a resonant sensor array may comprise one or more discretely addressable resonant sensors, each of which specifically binds a different cell surface molecule. Preferred cell populations for use in such methods are lymphocytes, which may be screened for the presence or amount of cells in each of a plurality of lymphocyte subsets (e.g., using antibodies specific for various CD or MHC markers immobilized to each resonant sensor); bacteria, which may be screened for the species and/or serotype of organisms present (e.g., using species- or serotype-specific antibodies immobilized to each resonant sensor), and phage, bacteria, or yeast display libraries (e.g., using antigens of interest immobilized to each resonant sensor). This list is not limiting, and the skilled artisan will understand that additional cell populations may be screened by the methods described herein.

The term "phage display library" refers to a plurality of phage, each comprising a nucleic acid encoding an exogenous polypeptide fused genetically to a polypeptide directing expression of the exogenous polypeptide on the phage surface. Typical commercially available phage display libraries include structured peptide libraries, protein libraries, antibody libraries, linear peptide libraries, and enzyme libraries. Similar display technologies exist using organisms such as yeast and bacteria to display polypeptides of interest.

The skilled artisan will understand that such methods and devices may be advantageously used to screen for one or more compounds that affect the phenotype of cells in a cell population. For example, samples obtained from a human or non-human subject may be compared before or after exposure of the subject to a treatment regimen for an effect on the phenotype of cells present in the sample; alternatively, cells in vitro may be contacted with one or more compounds being screened for the ability to cause particular cells in a population to expand (or reduce) in number relative to other cells in the population.

Resonant sensors or resonant sensor arrays may also be used for purposes of monitoring cell growth: The term "cell growth" in this context refers to an increase in cell number at or near a resonant membrane surface. In various embodiments, the resonant sensor or resonant sensor array may be used to detect cells growing free in solution (e.g., in a fermentor or in a roller bottle culture system) or cells growing on a surface (e.g., on the surface of a tissue culture system). In preferred embodiments, the sensor or sensor array may serve as a substrate surface upon which cells are grown. The term "substrate" in this context refers to a solid surface that acts as a support for cells. Cells may be grown directly upon this surface, or additional layers (e.g., hydrogels, feeder layers, etc.) may be placed between the surface and the cells.

In various embodiments, the resonant sensor mayor may not comprise a specific binding partner for the cells. In embodiments in which growth of cells in solution is monitored for example, growth in the solution may be monitored by measuring the density of cells near the resonant sensor(s) (by detecting a change in resonant frequency at a given sensor) without specific binding at the resonant sensor. Similarly, in those embodiments in which a resonant sensor or resonant sensor array is exposed to cells growing on the surface, a resonant sensor or resonant sensor array may provide a substrate on which the cells are grown. The extent of coverage of the array may be used to determine the extent of growth; that is, as a cell colony expands or decreases in size, changes in cell density at various portions of the array may be monitored by detecting a change in resonant frequency at a given sensor. The skilled artisan will understand that such methods and devices may be advantageously used to screen for one or more compounds that affect the growth of cells.

Resonant sensors or resonant sensor arrays may also be used for purposes of monitoring cell movements. The term "cell movements" as used herein refers to the movement of one or more individual cells at or near a resonant membrane surface. In various embodiments, the ability of various chemical or physical stimuli to induce or retard movement of cells may be monitored. In such embodiments, a resonant sensor or resonant sensor array may provide a substrate on which cells are maintained. The effect of one or more molecules (e.g., chemotactic molecules; chemotactic inhibitors) on cell movement may be monitored by detecting a change in resonant frequency at a given sensor.

Resonant sensors or resonant sensor arrays may also be used for purposes of monitoring the binding of cells to ligands for cell surface molecules, such as receptors. In various embodiments, a library of molecules comprising a plurality of different molecular species to be screened for the ability to bind to a particular cell surface molecule are immobilized at one or more resonant sensors. Preferably, each resonant sensor in an array comprises a different immobilized molecular species from the library. Cells expressing the cell surface molecule of interest are contacted with each resonant sensor, and the ability of one or more cells to bind to a given sensor via receptor/ligand interaction is monitored by detecting a change in resonant frequency.

Similarly, one or more inhibitors of ligand binding may be identified. In these embodiments, a library of molecules comprising a plurality of different molecular species to be screened for the ability to compete with ligand for binding at a particular cell surface molecule are immobilized at one or more resonant sensors. Preferably, each resonant sensor in an array comprises a different immobilized molecular species from the library. Cells expressing the cell surface molecule of interest are contacted with each resonant sensor in the presence of ligand, and the ability of one or more cells to bind to a given sensor via receptor/competitor interaction is monitored by detecting a change in resonant frequency.

In preferred embodiments, molecules that bind to a cell surface molecule may be ordered in terms of affinity for the cell surface molecule. In these embodiments, the number of cells contacted with a resonant sensor array may be reduced in steps, and the relative number of cells bound to each immobilized molecular species determined as a function of total cell number.

Preferred molecules for screening in such methods include small molecules, prodrugs, polypeptides, antibodies, antibody fragments, single-chain variable region fragments, polynucleotides, oligonucleotides, oligonucleotide analogs, oligosaccharides, polysaccharides, cyclic polypeptides, peptidomimetics, and aptamers.

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

As used herein, the term "polypeptide" refers to a covalent assembly comprising at least two monomeric amino acid units linked to adjacent amino acid units by amide bonds. An "oligopeptide" is a polypeptide comprising a short amino acid sequence (i.e., 2 to 10 amino acids). An oligopeptide is generally prepared by chemical synthesis or by fragmenting a larger polypeptide. Examples of polypeptide drugs include, but are not limited to, therapeutic antibodies, insulin, parathyroid hormone, polypeptide vaccines, and antibiotics such as vancomycin; Novel polypeptide drugs may be identified by, e.g., phage display methods.

As used herein, the term "polynucleotide" refers to molecule comprising a covalent assembly of nucleotides linked typically by phosphodiester bonds through the 3' and 5' hydroxyls of adjacent ribose units. An "oligonucleotide" is a polynucleotide comprising a short base sequence (i.e., 2 to 10 nucleotides). Polynucleotides include both RNA and DNA, may assume three-dimensional shapes such as hammerheads, dumbbells, etc., and may be single or double stranded. Polynucleotide drugs can include ribozymes, ribozymes, and polynucleotide vaccines.

As used herein, the term "oligonucleotide analog" refers to a molecule that mimics the structure and function of an oligonucleotide, but which is not a covalent assembly of nucleotides linked by phosphodiester bonds. Peptide nucleic acids, comprising purine and pyrimidine bases linked via a backbone linkage of N-(2-aminoethyl)-glycine units, is an example of an oligonucleotide analog.

The term "polysaccharide" as used herein refers to a carbohydrate comprising 2 or more covalently-linked saccharide units. An "oligosaccharide" is a polysaccharide comprising a short saccharide sequence (i.e., 2 to 10 saccharide units).

As used herein, the term "cyclic polypeptide" refers to a molecule comprising a covalent assembly of monomeric amino acid units, each of which is linked to at least two adjacent amino acid units by amide bonds to form a macrocycle.

As used herein, the term "peptidomimetic" refers to a molecule that mimics the structure and function of an polypeptide, but which is not a covalent assembly of amino acids linked by amide bonds. A peptoid, which is a polymer of N-substituted glycine units, is an example of a peptidomimetic.

The term "aptamer" as used herein refers to polynucleotides that bind to non-polynucleotide target molecules (e.g., a polypeptide or small molecule).

While aspects and embodiments of the present invention are described herein, it would be understood that such descriptions are exemplary of uses and aspects of the presently described sensors and arrays should not be limiting in content.

DETAILED DESCRIPTION

Figure 1:
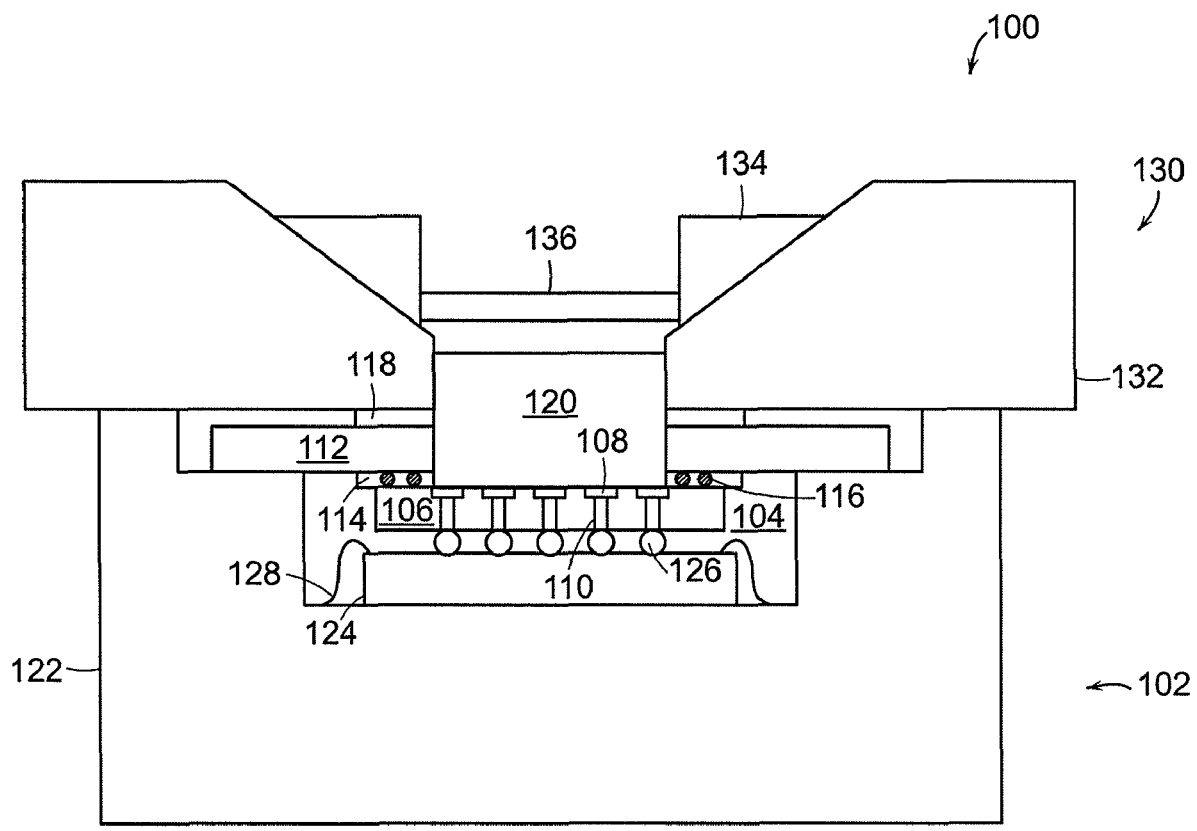
FIG. 1 is cross-sectional view of a sensor assembly according to an embodiment of the invention.

The present invention is generally directed to a variety of sensors, assemblies for such sensors and transmission and processing of signals from the sensors for analysis. The assemblies for the sensors provide improved performance of the sensors by providing a thermally insensitive environment and short pathways for signals to travel to processing components. Further, the assemblies provide modular construction for the sensors and housing modules, thereby allowing replacement of the sensors at a lower cost.

Resonant sensors are disclosed in U.S. patent application Ser. No. 09/845,521, entitled MICROFABRICATED ULTRASOUND ARRAY FOR USE AS RESONANT SENSORS, filed Apr. 26, 2001; and International Publication No. WO 02/25630, entitled MICROFABRICATED ULTRASOUND ARRAY FOR USE AS RESONANT SENSORS, published on Mar. 28, 2002, each of which is hereby incorporated by reference in its entirety. The disclosed sensor comprises at least two electrodes formed on a substrate having a cavity. Electrodes in the sensor cavity are preferably planar. The substrate may be doped with an impurity which, depending on the type of substrate chosen (p-type or n-type), can indicate either a substance such as boron, P-type, or phosphorus, N-type, to act as leads and/or electrodes. The electrodes of the sensor may also be formed of one or more metal or diffused dopant electrode layers in the bottom of the cavity.

Leads are used to connect electrodes to a power source or ground. The leads can be prepared by fabricating conductive vias through the substrate cavity which lead away from the cavity in a substantially perpendicular manner. Such perpendicular leads can be prepared to extend through the substrate to the exterior of the sensor in order to be connected to an electrical current source, or the leads can extend from the substrate cavity floor and be configured to exit the sensor at an angle, through one or more sides of the sensor itself.

Resonation or vibration of the membrane can be initiated electrostatically through use of electrodes in the sensor base, the membrane, the cavity wall, the cavity floor and/or membrane where the electrodes are connected in a manner that allows the initiation or creation of an electric current and/or potential. Resonation or vibration of the membrane of the sensor can be monitored using electrodes that can be located in and around the sensor as described and illustrated herein, and which can be part of a monitor apparatus, or monitoring can occur, for example, either acoustically, electronically by electromechanical transduction such as by electrostatics/capacitance, piezoresistance or piezoelectricity, or optically by interferometry, such as laser-Doppler vibrometery.

Sensor or sensor arrays also can be used to determine known or unknown analytes in a sample using direct and indirect binding, competitive inhibition, sensitivity testing, specificity testing, affinity determination, and the like. For example, indirect binding may be used when the amount of analyte that binds to the sensor membrane surface is too low for the sensor to detect. In this case, the sensor can be contacted with a sample containing a binding partner specific for the analyte bound to the sensor membrane. The sample-containing binding partner is preferably specific for site on the analyte that is separate and non overlapping from the site bound by the membrane immobilized binding partner such that the two binding partners can be bound simultaneously to a single analyte molecule. Thus, indirect detection is achieved when the additional mass attributed to binding of the sample containing binding partner to analyte on the membrane becomes detectable. Competitive inhibition may be used with a sensor or sensor array of the invention when an inhibitor analyte of lower mass inhibits binding of a larger mass analyte to the membrane.

Sensor Assembly

The present invention provides a sensor assembly for a resonant micromechanical membrane sensor, for example, that is sensitive to changes in the surface properties of the membrane surface such as density, inertia, viscous drag, or force. Measurement of a density change using the sensors of the present invention is particularly suited for the detection of molecular interactions in a gas or liquid phase environment at the membrane surface of the sensor. A feature of the sensor is a drum-like cavity comprising a membrane at the top which contacts the environment to be sensed, or more walls that support the membrane, and a base with at least one electrode. The harmonic response of the device is sensitive to the surface properties of the membrane. The membrane also protects the drive elements within the cavity from direct contact with the environment. The cavity also has other elements and various sensor embodiments will now be described in detail.

Figure I illustrates one embodiment of a sensor assembly according to the present invention. The sensor assembly 100 includes a housing assembly 102 and a sensor module 104 accommodated within the housing assembly 102. The sensor module 104 includes a sensor such as an ultrasound sensor 106. The ultrasound sensor 106 is provided with a plurality of sensing regions, each region corresponding to a cavity such as cavity 108. The cavities and the remaining structure of the sensors, such as sensor 106, are described below in further detail with respect to FIG. 2.

Referring again to FIG. 1, a conductive via, such as via 110, is provided within the sensor 106. The via 106 leads from the cavity 108 formed on the top surface of the sensor 106, to the bottom surface of the sensor 106. Each via 110 is adapted to conduct signals from the sensing regions above the cavities 108 to a signal processor. One method for constructing the vias 110 is described below with reference to FIGS. 3A-3G.

The sensor module further includes a nonconductive frame 112. The nonconductive frame may be formed of any of a number of nonconductive materials. Preferably, the nonconductive frame 112 is formed from an alumina card or other ceramic. In an alumina card, a region may be cut out to mount the sensor 106 therein. Ceramics such as alumina provide the advantage of extreme stability. For example, alumina has a very low co-efficient of thermal expansion, thereby resisting changes due to temperature changes. In this regard, the sensor 106 remains stable despite temperature changes in either the environment or in the sample solution. Further, ceramics such as alumina resist torsion or other deformities in the configuration and, therefore, provide positional stability for the sensors.

The nonconductive frame 112 may be attached to the sensor 106 in a variety of ways. In the disclosed embodiment, a nonconductive underfill 114 is provided around the perimeter of the sensor 106 to secure the sensor 106 to the nonconductive frame 112. The underfill may be made of any of a number of known materials that may function as insulators, for example. Solder balls 116 may be provided within the underfill 114 to provide a conductive path from the sensor 106 to leads (not shown) extending out of the sensor assembly 100. The leads may provide an electrical connection to a driving voltage for a membrane of the sensor.

Solder balls 116 may be shaped as barrels and may be embedded in the underfill on all sides. A second underfill 118 may be provided above the nonconductive frame 112 to provide support and insulation for additional modules.

The underfills 114 and 118 and the nonconductive frame 112 together form a sample reservoir 120 above the sensor 106. The sample reservoir 120 may be adapted to hold therein a sample such as liquid or a gel containing materials to be tested. In this regard, the reservoir 120 is electrically insulated from all electrical components, such as the electronics for the sensor.

In one embodiment, the entire sensor module 104, including the sensor 106, the nonconductive frame 112 and the underfills 114 and 118, may be discardable. In this regard, the sensor module 104 and the housing assembly 102 are made modular and interchangeable with other like components. For example, the same housing assembly 102 may be used with a variety of sensor modules such as sensor module 104. Thus, expensive electronics which may be included in the housing assembly 102 may be retained for reuse when a particular sensor module is to be discarded.

Housing assembly 102 includes a rigid housing 122 that may be made of a rigid material, such as ceramic. In one embodiment, the rigid housing 122 is made of a low-temperature co-fired ceramic (LTCC). This construction provides the housing with stability and resistance to temperature changes in the environment. Thus, a sensor module housed in the housing assembly is stabley supported. As above, the ceramic or LTCC also provides resistance to torsion or other deformities.

An electronic component 124 is mounted on the rigid housing 122 of the housing assembly 102. The electronic component 124 may be any component adapted to receive and/or process signals from the sensor 106. In one embodiment, the electronic component 124 is an amplifier for receiving the signals from the sensor 106 and transmitting the amplified signals to another processor. Alternatively, the amplifier may include circuitry for digitizing the signals and performing digital signal processing.

Gold studs 126 are provided on the electronic component 124 to provide electrical communication between the sensor 106 and the electronic component 124. The gold studs may be shaped to interface an off-the-shelf electronic component, such as an amplifier, to a customized sensor such as a MEMS. In this regard, the cost of the sensor assembly 100 may be decreased through the use of cheaper off-the-shelf components. In one embodiment, a silver filled epoxy may be used to complete the connection between the gold studs and the vias 110 of the sensor 106. Thus, the electronic component can be positioned adjacent to the sensor 106, and signals from the sensor cavities 108 are directed through a path of minimal length through the vias 110. In this configuration, unnecessary noise from an extended transmission path is eliminated. Signals are transmitted through the shortest path by transmitting them directly from the sensor cavities 108 through the vias to an electronic component such as an amplifier for processing of the signals.

The signals may be transmitted from the electronic component 124 to additional electronics outside the rigid housing 122. In this regard, wire leads 128 are provided to extend from the electronic component 124. The wire leads 128 may extend through the rigid housing 122 to a region outside the sensor assembly 100. In one embodiment, the rigid housing 122 may be constructed from layers of LTCC. The wire leads 128, then, may be directed between two layers through the rigid housing 122.

A fluidics module 130 may be provided to control the flow of a sample fluid through the sample reservoir 120. The illustrated embodiment of a fluidics module 130 includes a fluidics base 132, which is preferably formed of a rigid ceramic to provide thermal insensitivity and resistance to deformities. In one embodiment, the fluidic base is made of either alumina or glass. The fluidics base 132 may be provided with channels (not shown) for directing a fluid containing the sample to and from the sample reservoir 120. In this regard, a desired flow and a desired flow rate may be maintained within the reservoir 120. In the illustrated embodiment, an internal perimeter of the fluidics base 132 combines with the underfills 114 and 118 and the nonconductive frame 112 to form the reservoir 120.

The, fluidics module 130 may also include a window assembly. The window assembly includes a frame 134 which engages the fluidics base 132. The window assembly also includes a window 136 that can be positioned directly above the reservoir 120. The window 136 may be made of several materials including glass or sapphire.

Thus, the sensor assembly 100 provides a rigid self-supporting structure for the sensor operation. This self-supporting structure, preferably formed of a ceramic, allows a smaller package than may be feasible with other materials such as plastic. Further, the use of rigid materials such as ceramics inhibits vibrations or tortions of the sensor assembly, which may be a concern with plastic components. Further, the modular nature of the sensor assembly allows interchangeability of the various modules. As noted above, the sensor module 104 may be made discardable, while the housing assembly 102 and the fluidics module 130 may be reusable with other sensor modules. In this regard, a low-cost sensor assembly is achieved.

Still further, the arrangement illustrated in FIG. 1 provides the important benefit of reducing unnecessary noise in the signals. By providing a direct path through the vias from the sensor region of the sensor 106 to an electrical component through a via 110, a significant reduction in noise that may result from an extended conductive path is achieved.

Sensor Structure

Figure 2:
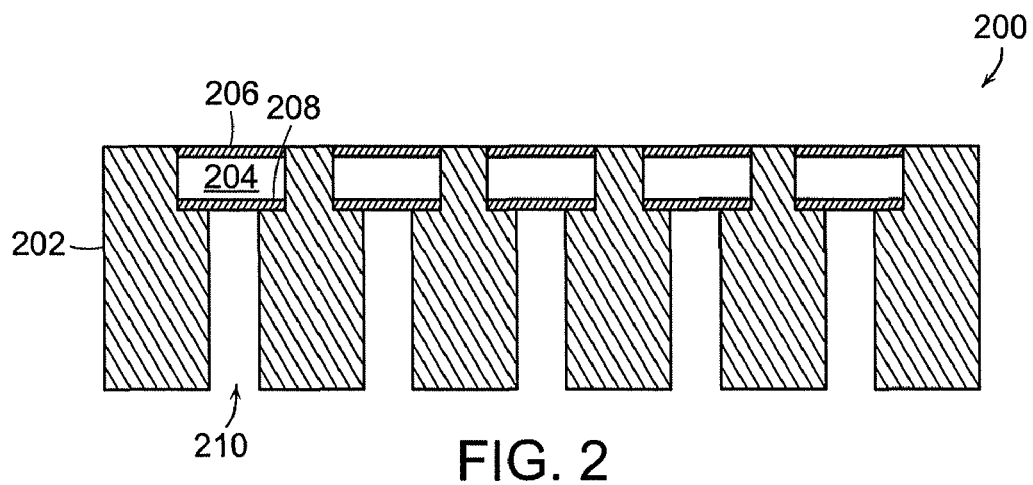
FIG. 2 is a cross-sectional view of an ultrasound sensor according to an embodiment of the invention.

Referring now to FIG. 2, an embodiment of a sensor element that may be used with the sensor assembly described in FIG. 1 will be described. The sensor element 200 is formed from a substrate 202. On one surface of the substrate 202, one or more cavities 204 may be formed. Each cavity is provided with a membrane 206 that also either forms or includes a first electrode for a capacitor. The first electrode may also serve as a lead to provide an input driving voltage to the membrane.

At the bottom of the cavity 204, a second electrode 208 is formed. Thus, the two electrodes 206, 208 in a spaced apart configuration form a capacitor. A sample solution may be provided above the membrane 206 and may include agents that may bind to the membrane 206. When such binding occurs, certain properties of the membrane 206 are altered. In this regard, characteristics such as the resonant frequency of the membrane are also altered. Thus, binding events may be detected through the detection of changes in resonant frequency of the membrane 206. In this regard, a driving frequency may be applied to the membrane 206 through an electronic source (not shown).

The substrate 202 is provided with a plurality of vias 210 extending from the bottom of each cavity 204 to the bottom surface of the substrate 202. The structure of the vias and possible variations therein are described below with reference to FIGS. 3A-3G.

Figure 3A:
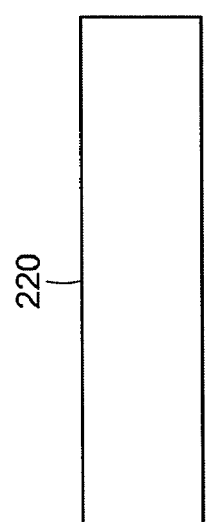
FIGS. 3A to 3H illustrate a process according to an embodiment of the present invention by which coaxial channels are formed in vias.
Figure 3B:
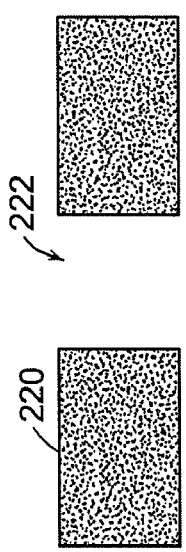

In FIGS. 3A-3G, one embodiment of a process for forming the vias in the substrate is illustrated. A substrate 220 is etched to have a via 222 formed completely therethrough (FIG. 3B). The via may be formed by any of a number of known etching methods such as laser etching using masks. Such methods are well known to those skilled in the art.

Figure 3C:
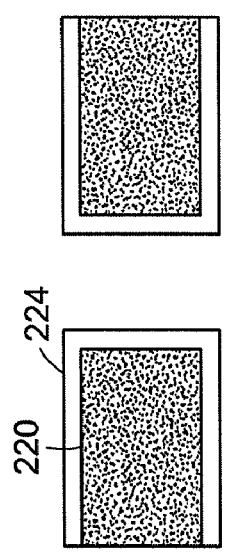

A conformal growth 224 is then deposited upon the substrate 220 (FIG. 3C). The conformal growth 224 may be made of any insulating material such as a number of oxides. The conformal growth layer 224 is formed on all surfaces of the substrate 220 including the walls of the via 222. A hollow channel through the via is maintained after the formation of the insulating layer 224 on the walls of the via.

Figure 3D:
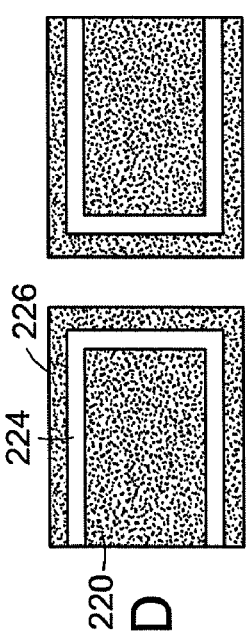

Next, a conductive layer 226 is formed on the conformal insulating layer 224 (FIG. 3D). The conductive layer 226 may be formed through several known methods including sputtering. In a preferred method, the conductive layer 226 is formed by first filling the via 222 with a conductive material, which could initially be in the form of a paste. Once the via 222 has been completely filled with the conductive material, an etching process may be performed to create an opening through the conductive layer 226.

Figure 3E:
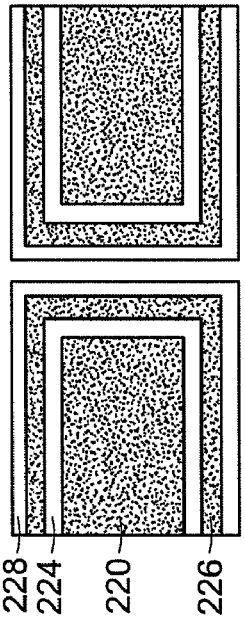

Next, a second layer of insulating material 228 may be formed through, for example, conformal growth (FIG. 3E). As above, the layer of insulating material 228 covers all surfaces including the walls of the via. Again, a hollow channel through the center of the via is maintained after the formation of the insulating layer 228.

Figure 3F:
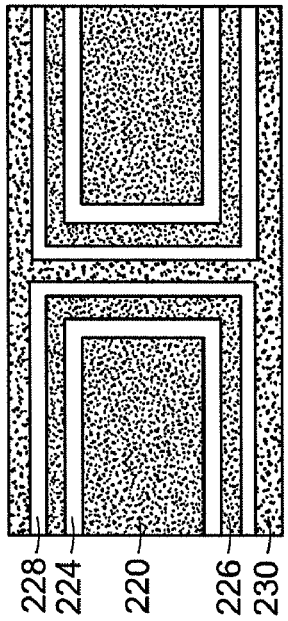
Figure 3G:
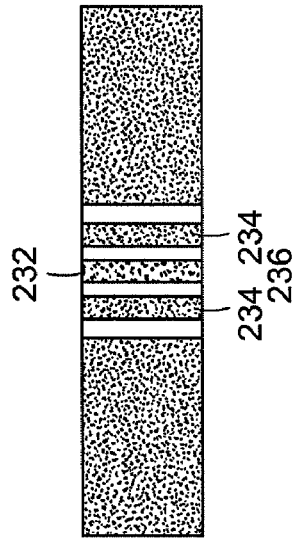

Next, as shown in FIG. 3F, a conductive material 230 is used to fill the hollow channel at the center of the via. The conductive material 230 fills the central region of the via and may also cover the top and bottom surfaces of the substrate or conformal growth thereon. Finally, the layers of insulating material and conductive material are removed from the top and bottom surfaces of the substrate (FIG. 3G). This may be performed in any number of ways including chemical cleaning or mechanical polishing.

Once the above-described process is completed, the substrate is left with a via having a plurality of coaxial channels. In the embodiment illustrated in FIG. 3G, two coaxial conductive channels, inner conductive channel 232, and outer conductive channel 234 are formed and are separated by insulation layers from each other and from the substrate.

Figure 3H:
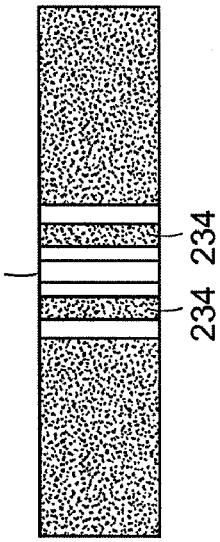

In another embodiment, the step described in FIG. 3F may be skipped. In this configuration, illustrated in FIG. 3H, the completed substrate is provided with coaxial channels including an outer conductive channel 234 and inner fluid channel 236, the hollowed central region of the via.

Thus, the formation of the coaxial vias can allow a sensor mounted on one surface of the substrate to provide an electrical connection to the opposite surface of the substrate. Thus, the sensor on top of the substrate can send signals through the shortest path to an electrical component on the bottom of the substrate.

Signal Detection and Processing

In a preferred embodiment, the system supports a 4×4 or 8×8 MEMS array of disk diaphragm on silicon. The system design demonstrates robustness to measure the resonant frequency shifts for single channel (1 Hz-100 Hz or so) and for scaling up the number of channels to a large number of channels. The MEMS designs provide the ability to: 1) enable large Q value in water, 2) allow electronic measurement of mechanical motion of the diaphragm by allowing it to be a significant percent of the gap between the electrodes (e.g., 40-160 nm for 1 um spacing for driving voltage of 5-10V for 20 um radius), and 3) provide low stray capacitance.

The through holes (vias) are made using controlled porous silicon (e.g. coherent pores) by an anisotropic etching. The advantage of this approach relative to die-to-die wire bonding is in the fact that one could achieve higher packaging density (3D stacking rather than 2D) and, thus, lower parasitics. Further, we can displace ASIC from the surface exposed to the chemo-biological solution environment to the bottom surface of the substrate or COB.

In essence, the through holes may be arranged to be integral-via design to the MEMS chip. Ultimately the holes would be metallized with the metal sleeve only, or may be filled with poly metal, and with less than 100 m-Ohms in-series DC resistance.

The theoretical model used to estimate transmission line parameters may be based on quasi-TEM model, since the conductivity and the dielectric between the throughhole contacts may be lossy. The effect of losses result in three major changes over the lossless case. The first change is that the forward and backward traveling waves suffer an attenuation as they move along the line. The second implication is that the forward-traveling voltage and current waves may no longer be in phase since Zc is complex. The third change occurs in the velocity of propagation of the voltage and current waves.

The following was the standard set of lossy dielectric-lossy-conductor formula used for this calculation:

$$R(\Omega/m) = 1/(pi * a * \delta * \sigma_C); (\delta \Box a)$$

$$L(H/m) = \frac{\mu}{\pi} * \cosh^{-1}\frac{d}{2*a}$$

$$G(1/\Omega * m) = \frac{\pi\sigma}{\cosh^{-1}\frac{d}{2a}}$$

$$C(F/m) = \frac{\pi\varepsilon}{\cosh^{-1}\frac{d}{2a}}$$

where:

$$\delta = \frac{1}{\sqrt{\pi f \mu_C \sigma_C}} = \text{skin\_depth}$$

where:

$\sigma_C, \mu_C, \in_C = \in_0$ are conductor-specific resistance, magnetic permeability, and dielectric constant, respectively, and where:

$\sigma, \mu, \in$ are characteristics of the dielectric that separates them.

The calculation above is applied on 10-, 15- and 20-μm diameter of the contact holes with oxide lined at the inner side (insulation) and filled with a poly silicon (approximate Poly through hole filler conductivity based on (0.0006 to 0.0050) Ohms-cm). All further specific example calculations are based on value of 0.3 mOhms-cm.

The total thickness of the wafer used in calculations is 300 m. Bump calculation includes physical data parasitics gathered from different flip-chip and CSP/WSP packaging manufacturers (e.g., Kullicke & Soffa and Amkor Technologies).

Drum device radius design varies between 10-, 20- and 30-μm with the approximate spacing of 1 μm and membrane thickness of 1000-2000 angstroms. Measurements have shown membrane displacement from 10-50 nm for 20-40 Volts.

The initial spacing estimate does not include any external force (e.g., pressure differential or water pressure on the membrane) or non-linearity of the restoring nor damping force. The distance between the electrodes for the device in equilibrium could be found from force-balance equation or static capacitance measurements (providing that we know, restoring force and electrostatic force). However, for modeling purposes, a simple parallel plate capacitance with one free electrode and one fixed electrode is used.

Figure 7:
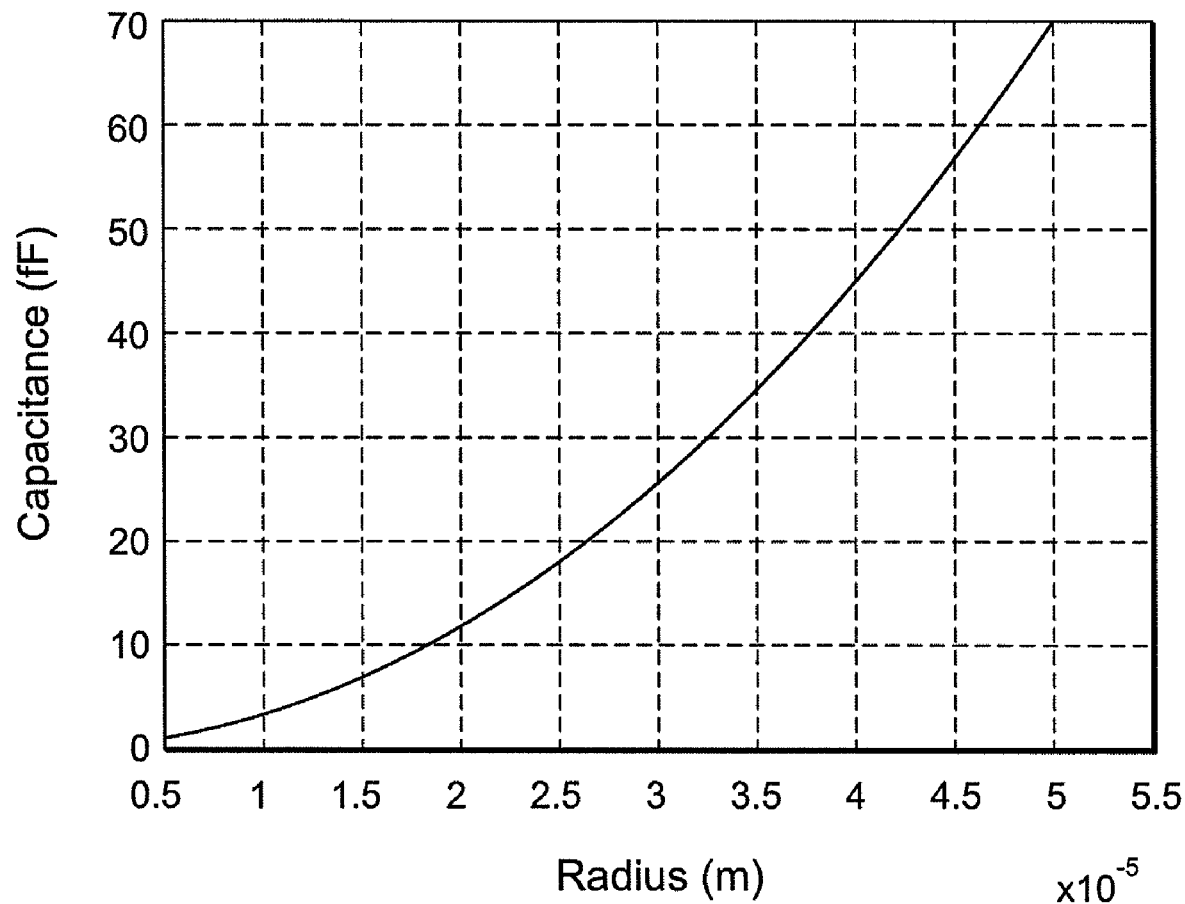
FIG. 7 is a chart illustrating the capacitance as a function of the radius of a membrane.

FIG. 7 shows capacitance as a function of radius of the membrane. As seen in FIG. 7, the equilibrium capacitance corresponding to the 10-, 20- and 30-m radius are C10=2.78 fF, C20=11.12 fF, and C30=25.02 fF, respectively.

The bottom electrode may be highly n-doped silicon in 30 KOhm-cm highly resistive n-type wafer pool. The preferred MEMS design electrode is not insulated from the rest of the wafer electrically. This could imply that instead of grounding the substrate, one could connect the substrate to the output where it would represent shield connected to the output of the buffer amplifier (in AC voltage divider topology). Thus, we would remove parasitics from the shield. This also would imply that we would have to ground bottom electrode instead of top and have $V_{drive}$ delivered to the top electrode.

If the bottom electrode is at the high potential, one would need to connect substrate (wafer) to the ground. However, the noise susceptibility of the top electrode would be elevated since the grounded top electrode would be affected by any electrical noise that is coming from the chemistry (polarization, electrical dipole effects and water capacitor effects if any –tbd). Minimal electrical potential at this electrode would effect the measurements. Furthermore the top electrode (only 1000-2000 Angstrom's), if it is on a high potential and exposed to the liquid, will require insulation relative to the liquid above. The thickness of highly doped silicon membrane is way below the skin depth thickness at the potential frequency of the operation and for the conductivity achieved by the doped silicon. Therefore, total shield effectiveness should be taken into consideration. In addition, whichever end is grounded (the top or the bottom plate capacitor) should be included in parasitics.

Traditional low-capacitance sensors have used conventional amplifiers with integrated buffers and op-amps. These amplifiers are effective for sensors operating at relatively large sensing capacitance. However, many sensors, including sensors that may be used with the sensor assembly described above, operate at much lower sensing capacitances of several ato-Farads ($10^{-18}$), for example. At such low sensing capacitances, parasitic capacitance well above the 1 pico-Farad level can attenuate the signal below the noise level. Further, many traditional amplifiers require a larger footprint than may be desirable for use in small sensors which may be placed in an array. The size of the amplifier may cause the sensors in the array to be more spaced apart than either necessary or desirable.

Figure 4A:
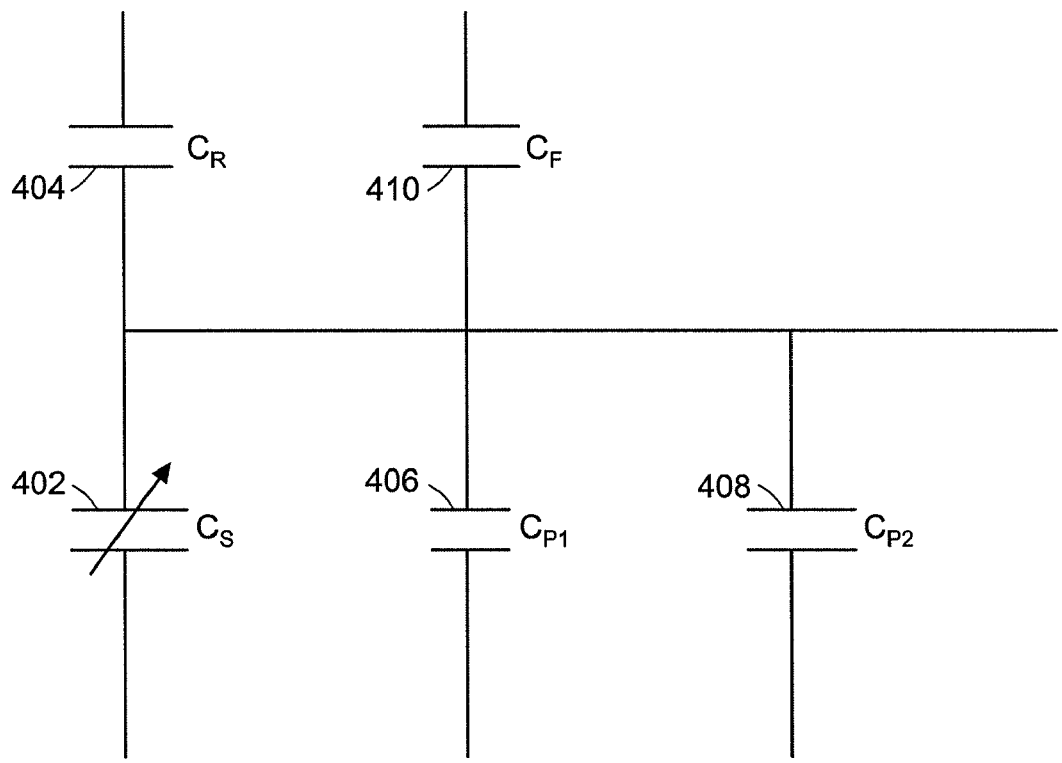
FIG. 4A is a schematic illustrating the various capacitances which may exist in an electronic component receiving signals from the sensor.

FIG. 4A illustrates the various capacitances which may arise in an electronic component such as a pre-amplifier or an amplifier. In addition to the primary capacitance being detected form the sensor, $C_S$ 402, a reference capacitance $C_R$ 404 is provided to provide a baseline for detecting the sensed capacitance. The reference capacitance is generally selected to isolate the changes in the sensor capacitance in the presence of parasitic capacitances, as described below.

Parasitic capacitances may arise from several sources. In general, the addition of any electronic component may be accompanied with parasitic capacitances. For example, one parasitic capacitance, $C_{P1}$ 406, may arise simply from the sensor itself. This may be caused by, for example, the flowing of the sample fluid above the membrane. Additional parasitic capacitance, $C_{P2}$ 408, may arise from the implementation of the electronic component itself. The interconnection of the various components in a pre-amplifier or an amplifier (such as those described below with reference to FIGS. 4B-4D) may cause a parasitic capacitance to arise. Finally, a particular type of parasitic capacitance, called a Miller Capacitance, or $C_F$ 410, may be intrinsic to certain components such as MOSFET gates.

Figure 4B:
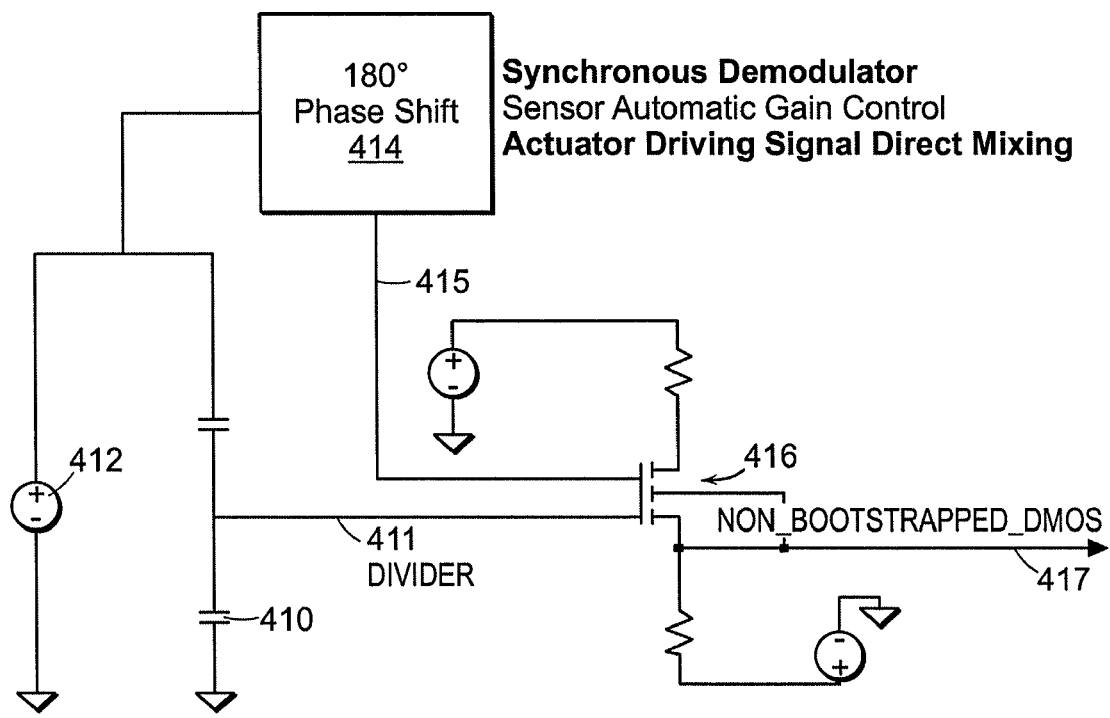
FIGS. 4B-4D are schematic illustrations of embodiments of an electronic component for processing of signals from a sensor such as the sensor illustrated in FIG. 1.

FIG. 4B is a schematic illustration of one embodiment of an amplifier for use with the sensors described above. In this embodiment, the drive signal for the membrane, which may be substantially greater than the response signal from the membrane itself, is separated using a dual-gate (MOSFET), or a lateral DMOS, and a phase-shifted drive signal. A dual gate FET, or MOSFET, is desirable for use in this arrangement due to its lower input capacitance relative to conventional amplifiers. Since the signals from the sensors are typically low-capacitance signals, this characteristic of MOSFETs improves the ability to process a measurable signal.

In this configuration, a drive signal is generated by an AC voltage driver 412. The drive signal drives the sensor capacitance 410 to generate a sensor capacitance signal that is indicative of the resonant frequency of the membrane. The signal that is output from the sensor (line 411) is a the response signal superimposed on the drive signal. In this regard, the drive signal is substantially greater in amplitude than the response signal. Thus, even a high signal-to-noise ratio may be insufficient to isolate the response signal.

The drive signal from the voltage driver 412 is also transmitted to a synchronous demodulator 414, which shifts the signal by 180 degrees. The synchronous demodulator 414 may be implemented in a variety of ways including through the use of a conventional phase-locked loop which is adapted to generate a signal that is 180 degrees out of phase. Thus, the output signal from the demodulator 414 is exactly 180 degrees out of phase with the drive signal and is transmitted through line 415.

A dual gate MOSFET 416 or a lateral DMOS is provided to receive the signals from the sensor capacitance 410 and the demodulator 414 (lines 415 and 411 respectively). The dual gate directly mixes the two signals and outputs the response to another component or sub-component for analysis (line 417). Thus, the large drive voltage component is exactly removed from the signal, providing only the membrane response signal. The response is substantially similar to the membrane response.

In an alternative embodiment, one can adjust the signal level of the demodulator signal to maximize the membrane response signal. Because of variations between different sensors and variations during operation, the desired demodulator signal level can be automatically determined either by a feedback circuitry or by a microprocessor. This circuitry effectively serves as an automatic gain controller (AGC), and can facilitate maximization of signal quality.

Figure 4C:
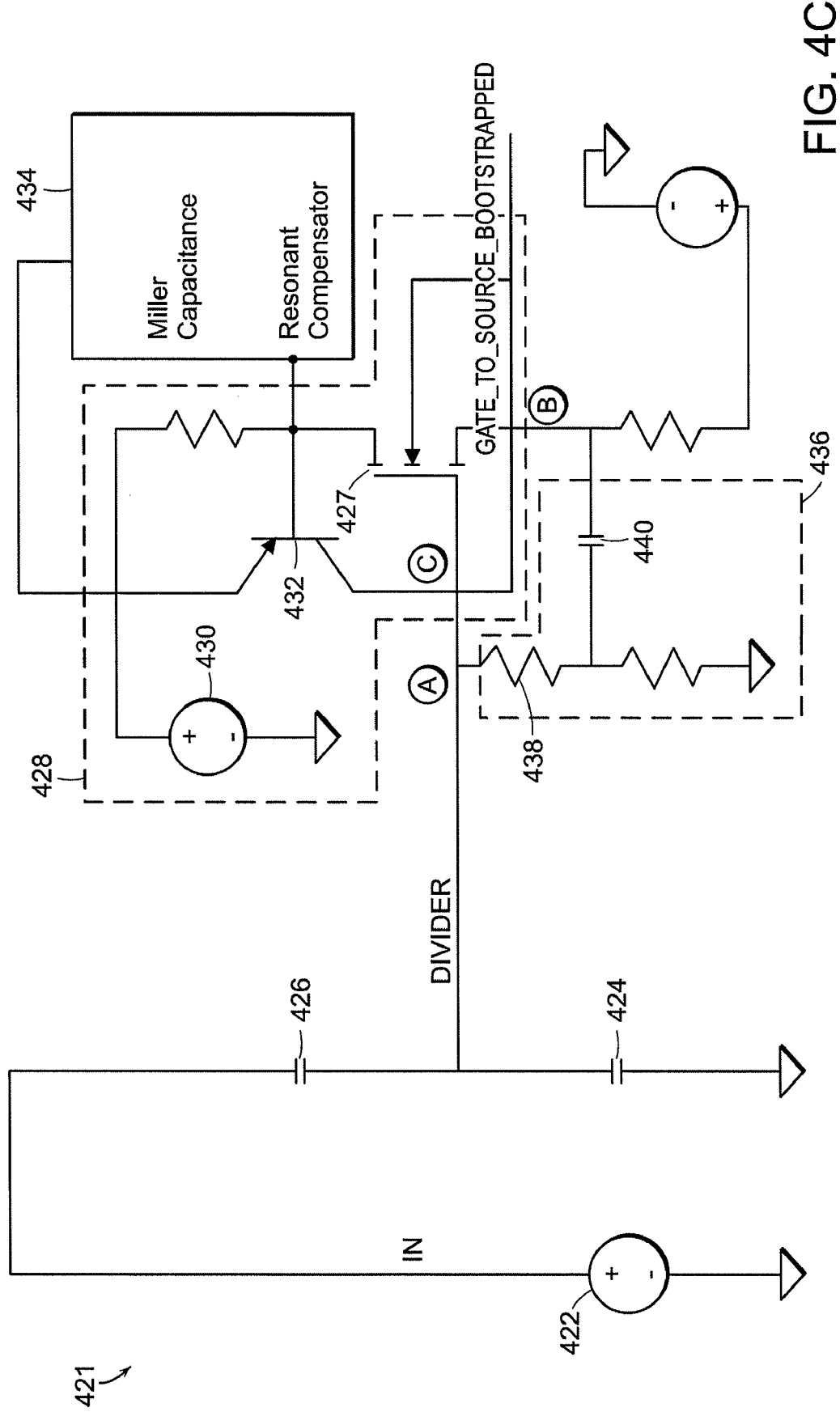

In another embodiment, shown schematically in FIG. 4C, the pre-amplifier 421 compensates for parasitic capacitances and Miller capacitance through bootstrapping. In this arrangement, an AC voltage driver 422 is provided to drive the membrane of the sensor 424. A reference capacitance 426 is again provided to facilitate isolation of the response signal. The output response from the sensor is directed to a dual gate MOSFET 427 or a lateral DMOS. Thus, at the point labeled "A" in FIG. 4C, the signal is the response signal from the sensor superimposed on the drive signal from the voltage driver 422.

At the point labeled "C" in FIG. 4C, the signal at point "A" is also directed to a phase compensation stage 428. The phase compensation stage 428 includes a DC voltage drive 430 for driving a transistor 432. The signal from the transistor 432 is directed to the dual-gate MOSFET 427 or a lateral DMOS through the point labeled "B". The phase compensation stage 428 then functions to maintain an identical signal at the point "B" as at point "A" though gate-to-source bootstrapping. Thus, the output signal is phase-matched to the sensor response signal.

An impedance matching stage 436 may also be provided to improve the amplitude matching of the output signal to the sensor response signal. The impedance matching stage illustrated in FIG. 4C includes a resistor 438 and a capacitor 440 through which a portion of the sensor response signal superimposed on the drive signal is directed.

Further, a Miller capacitance compensation stage 434 may be provided to facilitate compensation of the Miller capacitance in the signal. The Miller capacitance stage 434 is more clearly illustrated in FIG. 4D. As illustrated in the schematic illustration, the Miller capacitance stage is again gate-to-source bootstrapped through the phase compensation stage 428. In this regard, this configuration may be considered to be double bootstrapped and is capable of compensating all parasitic capacitances, including the Miller capacitance resulting from the use of the dual-gate MOSFET 427.

Figure 4D:
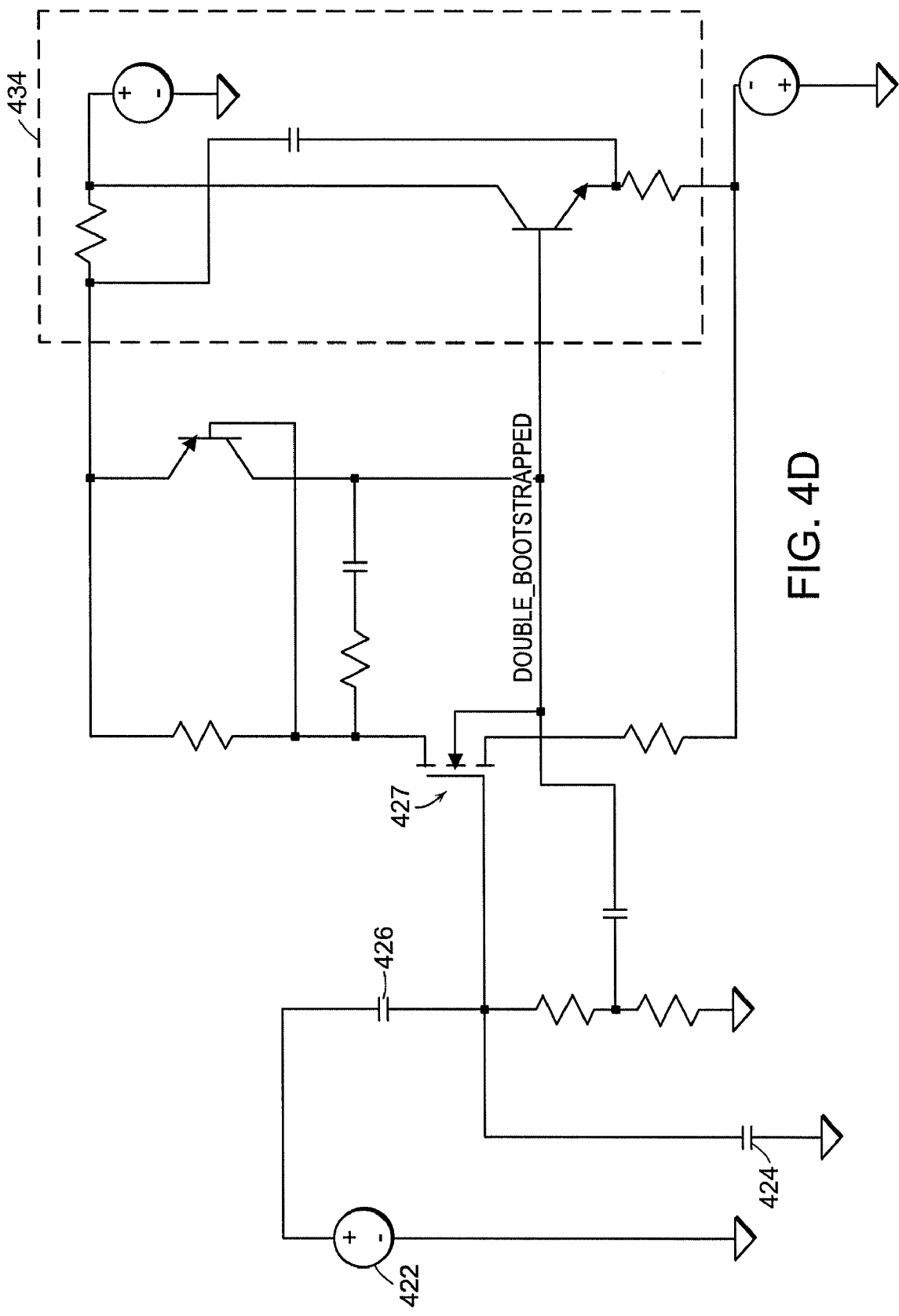

Accordingly, the embodiments of the electronic component described with reference to FIG. 4B-4D can provide a signal that contains no parasitics with the drive signal removed. Thus, the output of the component includes a sensor response signal with little or no parasitic components. Combined with the short path length from the sensor to the component, a signal with low noise level can be achieved.

Alternatively, the membrane can be actuated with a narrow pulse with a pulse duration significantly smaller than 'the period of the membrane vibration. Because the membrane typically vibrates for many periods, this actuation mode naturally separates sensor response to the drive signal.

The response received from the sensor with pulse excitation is generally a transient response which may be sampled at a high frequency. In his regard, the determination of the resonant frequency may be difficult from a low-Q sensor that may be used in the above-described arrangement. In these cases, the power of the response signal may vary greatly over the sampled time. As a result of the varying power, the signal-to-noise ratio also varies greatly.

Existing analysis algorithms for use with such sensors require computation of a correlation matrix to isolate the resonant frequency. Calculation of the matrix, however, can be very intensive and time-consuming, particularly where large data samples are gathered. Further, many existing algorithms are unable to isolate a second peak in the power-frequency profile of the received signal. In other words, these algorithms may be unable to identify the proper resonant frequency if another similar-powered frequency is present.

Periodograms are a search technique based on discrete Fourier transform of input or measured values. The classic periodogram is defined as a discrete sum:

$$\frac{1}{N}\left|\sum_{n=0}^{N-1} x(n)e^{-i\omega T}\right|^2;$$

where x(n) is an impulse response of the resonator, ω is angular frequency, and T is a selected sample period.

The above periodogram formula allows one to estimate the power of a signal at a specific frequency. By using a typical optimization technique (e.g., golden-ratio optimization), one can identify the maximum frequency of the capacitive sensor precisely with the application of the above formula at only a small number of different frequencies. This feature compares favorably with some of the "global" techniques that calculate the entire power spectrum.

Periodograms are generally not recommended for applications requiring high spectral resolution due to lack of accuracy. However, since the present embodiment seeks to detect only the differences in the resonant frequency, not the resonant frequency itself, the desired characteristic is precision, not accuracy. In fact, periodograms provide extremely good precision for resonant frequency calculations.

However, with a greatly varying signal-to-noise ratio, the noise level may sometimes have a bigger impact on the periodogram calculation than the actual signal. In other words, if only a portion of the measurement period contains the response signal and the remaining period contains either noise or extraneous signals, the measured response signal will be outweighed by the other components in the final periodogram sum. For example, the impulse response for a low-Q resonator quickly sinks below the noise floor. Thus, the signal at the earlier time is a better indicator of the resonant frequency than the later time.

A solution to this problem is achieved by including a time-dependant component to the classical periodogram. For example, the periodogram may be modified as follows:

$$\frac{1}{N}\left|\sum_{n=0}^{N-1} x(n)e^{-\alpha nT}e^{-i\omega T}\right|^2.$$

In this manner, a time-decay component is added to the periodogram. The time-decay component provides a weighting to the samplings as signal-to-noise ratio deteriorates. In the above equation, α is a constant that may be empirically determined.

Figure 5:
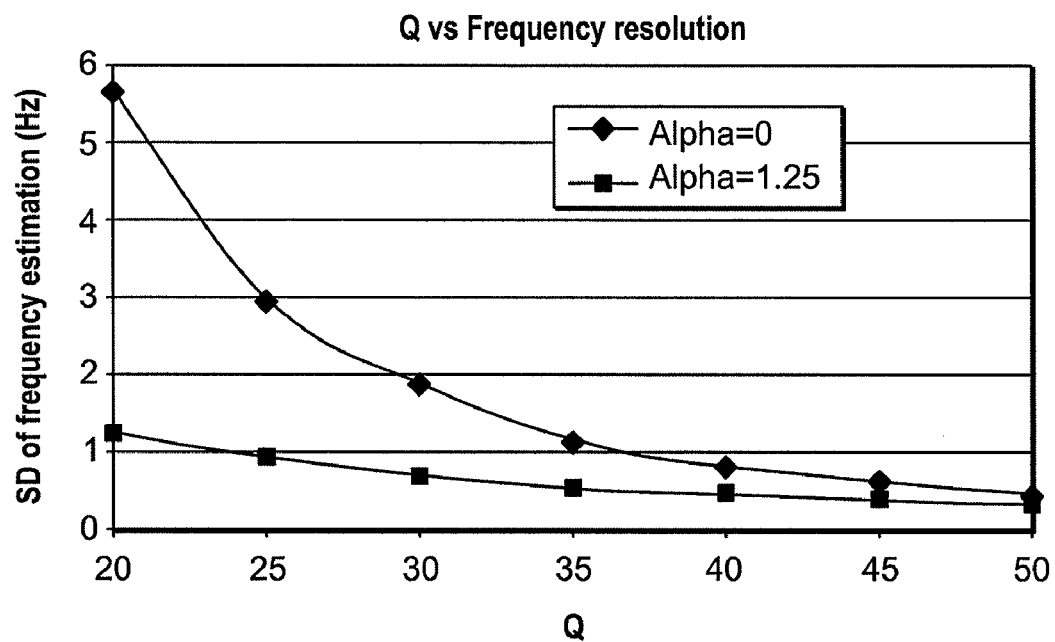
FIG. 5 is a graph illustrating standard deviation as a function of Q for signals processed using a standard periodogram versus a modified periodogram according to the present invention.
Figure 6:
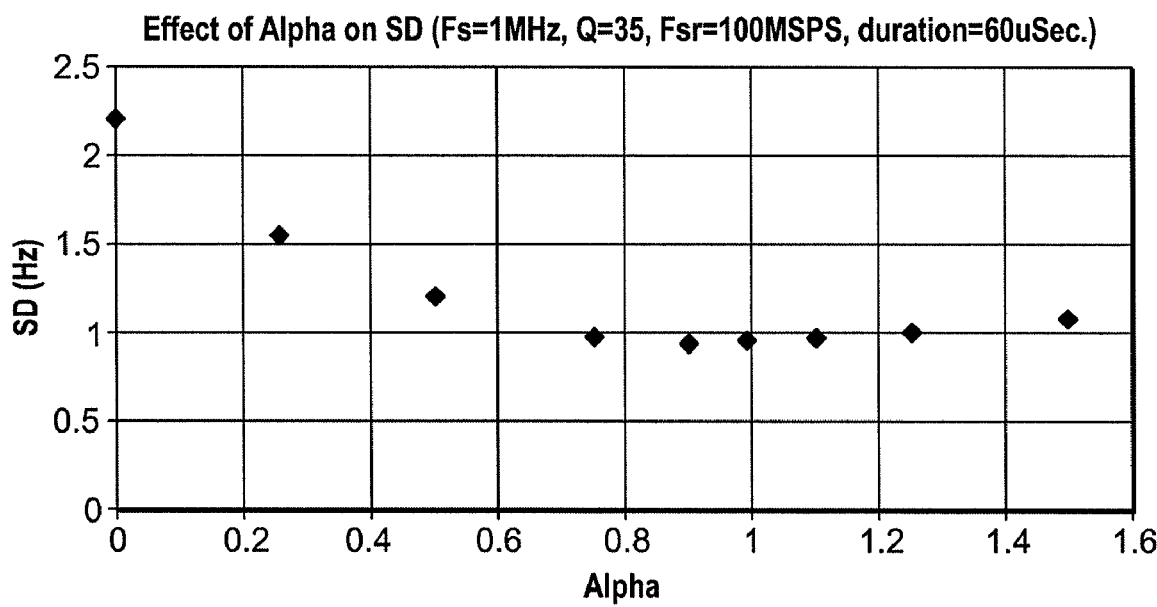
FIG. 6 is a graph illustrating standard deviation as a function of the sensor-specific constant alpha for use with a modified periodogram.

FIGS. 5 and 6 illustrate the effectiveness of the modified periodogram noted above. FIG. 5 shows comparisons between analyses using a classical periodogram (Alpha=0) and a modified periodogram with an α of 1.25. An effective measure of spectral analysis is the standard deviation achieved. Ideally, a very low standard deviation is desired. As shown in FIG. 5, the modified periodogram outperforms the classical periodogram for all values of Q. In fact, the advantages of the modified periodogram over the classical periodogram become particularly significant at low Q values.

Although the selected value of α should be empirically determined, FIG. 6 demonstrates that the value need not be precisely calculated. The standard deviation resulting from a modified periodogram analysis does not substantially change over a large range of values of α. For example, between α values of 0.75 and 1.25, the standard deviation achieved is substantially constant.

Applications for Use of Resonant Sensor Devices

As described in U.S. patent application Ser. No. 09/845,521, entitled MICROFABRICATED ULTRASOUND ARRAY FOR USE AS RESONANT SENSORS, filed Apr. 26, 2001; and International Publication No. WO 02/25630, entitled MICROFABRICATED ULTRASOUND ARRAY FOR USE AS RESONANT SENSORS, published on Mar. 28, 2002, resonant sensors and resonant sensor arrays may be used for monitoring a change in surface properties of a sensor membrane resulting from a binding event that changes the physical characteristics of the membrane surface, such as surface mass, viscous coupling, membrane stiffness, and the like.

The frequency of membrane resonance in such sensors is also sensitive to changes in mass in a geometric region above the sensor. As noted above, the shape of this geometric region may be approximated by a sphere having a diameter equal to that of the diameter of the membrane of the sensor. Thus, the area queried extends in the z axis dimension perpendicular to the plane of the membrane, and the sensor may be employed to sense differences in density within this region. As a result, the quantity of material passing near the sensor may be detected by a change in resonant frequency of the sensor membrane.

For non-affinity based sensing, the density of particles coming within the sensed volume can be monitored without a need for surface immobilization. The relative number or density of cells coming within this sensed volume could be used to monitor cell growth, either in solution (e.g., in a fermentor) or in cells requiring surface attachment (e.g., using the sensor or sensor array as a substrate to provide the required attachment support. In these embodiments, a resonant sensor or sensor array may be used to identify molecules that have an effect (positive or negative) on cell growth. For example, bacteria, tumor cells, normal cells, etc., may be grown on the surface of a sensor array, in which local regions of the array comprise growth enhancing or retarding compounds embedded in a hydrogel layer overlying the resonant sensor membrane(s). Selective growth would confer a density shift which would be detected by the sensor. Similarly, the chemotactic effects of factors immobilized to the surface of the sensor may be monitored by detecting changes or gradients in concentrations of cells drawn selectively to a given sensor. Such methods could be used to identify or assay chemokines or mitogens for example, or in wound healing models. Such sensors may also serve as mass sensors for an electrophoretic or chromatographic separation methods to provide continuous real time sensing over a broad area, such as might be used in either capillary electrophoresis or 1- or 2-dimensional electrophoresis.

The skilled artisan will recognize that such methods are not limited to biological applications, and that the "deep query" feature of resonant sensors and sensor arrays may be used generally as a density sensor for liquid compositions. For example, particulate material in solutions could be monitored in manufacturing processes, in waste water treatment, in plant exhaust gas emissions, in automotive emissions, or in slurrys. Likewise, changes in density in fluids caused by nonparticulate changes (e.g., changes in salinity or total dissolved solids) can also be monitored generally.

The term "dense particle" as used herein refers to a particle that has a density greater than that of the surrounding fluid medium, while the term "buoyant particle" refers to a particle that has a density less than or equal to that of the surrounding fluid medium. The term "liquid environment" as used herein refers to freely flowing liquid environments and any medium comprising water molecules within a solid or semisolid matrix. Examples of non-freely flowing liquid environments include gels (e.g., polyacrylamide, agarose, starch, hydrogel, etc.), cell interiors, chromatographic media, etc. This list is not meant to be limiting.

For affinity based sensing, a binding partner for a molecule of interest must be immobilized either at the resonant membrane surface, or sufficiently near to the surface so that a binding event will result in a change of density within the sensed region. Numerous methods have been described for immobilizing a molecule on a surface. For example, a physical interaction that provides a direct contact of the molecule of interest with the surface, such as adsorption, can be used. Additionally, a chemical interaction that results in ionic or covalent cross-linking of the molecule to the surface can also be used. For example, U.S. Pat. No. 4,284,553, which is hereby incorporated by reference, including all tables, figures and claims, discloses method for the covalent immobilization of protein molecules to oxide surfaces via thioester-containing coupling chains.

Alternatively, the molecule of interest may be indirectly immobilized on the solid surface. See, e.g., U.S. Pat. Nos. 6,171,610; 6,156,572; 6,048,548; 6,039,977; 5,902,603; 4,452,892, each of which is hereby incorporated by reference, including all tables, figures and claims; which describe methods of indirect immobilization, for example, by "enmeshing" or physically embedding a hydrogel comprising the molecule into a support surface, such as mesh cloth, or porous or roughened surfaces.

Molecules of interest in the methods described herein may include small molecules, polypeptides, proteins, cyclic polypeptides, peptidomimetics, aptamers, antibodies, scFvs, polysaccharides, receptors, polynucleotides, and/or polynucleotide analogs; and may include therapeutic drugs, pathogens, biological agents, environmental toxins, etc.

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

As used herein, the term "polypeptide" refers to a covalent assembly comprising at least two monomeric amino acid units linked to adjacent amino acid units by amide bonds. An "oligopeptide" is a polypeptide comprising a short amino acid sequence (i.e., 2 to 10 amino acids). An oligopeptide is generally prepared by chemical synthesis or by fragmenting a larger polypeptide. Examples of polypeptide drugs include, but are not limited to, therapeutic antibodies, insulin, parathyroid hormone, polypeptide vaccines, and antibiotics such as vancomycin. Novel polypeptide drugs may be identified by, e.g., phage display methods.

As used herein, the term "antibody" refers to an immunoglobulin molecule obtained by in vitro or in vivo generation of an immunogenic response, and includes both polyclonal, monospecific and monoclonal antibodies, and antigen binding fragments thereof (e.g., Fab fragments). An "immunogenic response" is one that results in the production of antibodies directed to one or more proteins after the appropriate cells have been contacted with such proteins, or polypeptide derivatives thereof, in a manner such that one or more portions of the protein function as epitopes.

As used herein, the term "single-chain variable region fragment" or "scFv" refers to a variable, antigen-binding determinative region of a single antibody light chain and antibody heavy chain linked together by a covalent linkage having a length sufficient to allow the light and heavy chain portions to form an antigen binding site. Such a linker may be as short as a covalent bond; preferred linkers are from 2 to 50 amino acids, and more preferably from 5 to 25 amino acids.

As used herein, the term "polynucleotide" refers to molecule comprising a covalent assembly of nucleotides linked typically by phosphodiester bonds through the 3' and 5' hydroxyls of adjacent ribose units. An "oligonucleotide" is a polynucleotide comprising a short base sequence (i.e., 2 to 10 nucleotides). Polynucleotides include both RNA and DNA, may assume three-dimensional shapes such as hammerheads, dumbbells, etc., and may be single or double stranded. Polynucleotide drugs can include ribozymes, ribozymes, and polynucleotide vaccines.

As used herein, the term "polynucleotide analog" refers to a molecule that mimics the structure and function of an polynucleotide, but which is not a covalent assembly of nucleotides linked by phosphodiester bonds. Peptide nucleic acids, comprising purine and pyrimidine bases linked via a backbone linkage of N-(2-aminoethyl)-glycine units, is an example of an oligonucleotide analog.

The term "polysaccharide" as used herein refers to a carbohydrate comprising 2 or more covalently-linked saccharide units. An "oligosaccharide" is a polysaccharide comprising a short saccharide sequence (i.e., 2 to 10 saccharide units).

As used herein, the term "cyclic polypeptide" refers to a molecule comprising a covalent assembly of monomeric amino acid units, each of which is linked to at least two adjacent amino acid units by amide bonds to form a macrocycle.

As used herein, the term "peptidomimetic" refers to a molecule that mimics the structure and function of a polypeptide, but which is not a covalent assembly of amino acids linked by amide bonds. A peptoid, which is a polymer of N-substituted glycine units, is an example of a peptidomimetic.

The term "aptamer" as used herein refers to polynucleotides that bind to nonpolynucleotide target molecules (e.g., a polypeptide or small molecule).

The term "therapeutic" or "drug" as used herein refers to molecules or compositions used in the treatment or prevention of disease.

The term "pathogen" as used herein refers to agents that cause disease, including bacteria and viruses.

The term "biological agent" as used herein refers to one or more molecules obtained from an organism.

The term "environmental toxin" as used herein refers to one or more molecules that is a poisonous to one or more functions of a cell, and that are present in the terrestrial environment.

U.S. patent application Ser. No. 10/306,506 (filed Nov. 26, 2002), which is hereby incorporated by reference in its entirety, describes methods and compositions for the immobilization of molecules at a surface in a biologically relevant aqueous or semi-aqueous environment, such as a water-swellable hydrogel. These methods allow molecules within the hydrogel to freely interact with other molecules, and can mimic a biological environment. Once immobilized to a surface via a hydrogel, the molecule(s) can be used as an immobilized binding partner. Such an immobilized molecule can, for example, be contacted with a test sample to determine if the sample contains a binding partner for the immobilized molecule. The methods and compositions can also be used in a microscale environment, such as at the surface of a resonant sensor membrane.

Affinity based resonant sensors and sensor arrays may be employed in methods analogous to numerous analyte binding assays well known to those of skill in the art. These include competitive and noncompetitive (e.g. sandwich) immunoassay formats, nucleic acid hybridization assays, etc. Advantageously, detection of a binding result is determined directly; that is, a change in mass or density at or near the resonant membrane resulting solely from analyte binding to an immobilized affinity partner is sufficient to cause a detectable change in resonant frequency. However, amplification methods may be employed to enhance the change in resonant frequency. For example, an analyte bound to an immobilized affinity partner may be further contacted with a second affinity partner to form an affinity partner-analyte-second affinity partner "sandwich." The second affinity partner may be conjugated to a mass enhancement moiety, such as a latex or metallic (e.g., gold) micro- or nano-particle, or an enzyme that catalyzes the deposition of a precipitate. Enzymes that are useful for this amplification purpose include glucose oxidase, galactosidase peroxidase, alkaline phosphatase, and the like. Further, enzymes that elongate the detected species, such as polymerases for DNA may be used. In particular, nucleic acid amplification methods such as strand displacement amplification, rolling circle amplification, isothermic methods such as "nucleic acid based sequence amplification ("NASBA"), or polymerase chain reaction ("PCR") may be used. These methods may be used as anchored or non-anchored procedures. The addition of this additional mass within the sensed volume can provide an enhanced resonance signal in the device.

In addition to the detection of the presence and/or amount of analytes such as proteins, small molecules, nucleic acids, etc., the "deep query" property of resonant sensors and sensor arrays allows the incorporation of 3-dimensional hydrogels onto the surface of the sensor(s) and/or allows the measurement of changes in the local density of microparticles such as vesicles or cells. The ability to detect binding interactions on the surface of intact cells has many advantages. Membrane embedded proteins (e.g. 7 transmembrane-family receptors or ion channels), are difficult to extract from membrane while still preserving native function. This occurs for several reasons. The proteins usually require a lipid component to retain native conformation and it is difficult to devise a solubilization protocol which preserves this, requiring optimization for each receptor. Further, part of the specificity of these receptors is derived from protein-protein interactions which only occur in the native membrane. For the binding of a transmembrane receptor to its ligand may be increased 100 fold or more by association with its normal heterotrimeric G-protein partner. It has also been suggested that numerous receptors may function as heterodimers.

The array format enables the determination of cellular attachment to and dissociation from immobilized molecules to be performed in parallel. Moreover, the ability to directly sense binding reactions allows real-time monitoring of cellular attachment and dissociation for one or many cells on an individual sensor surface. This capability can be applied to characterizing cell populations, e.g., for diagnostic purposes. For example, A/B/O antigens on erythrocytes could be rapidly identified in a blood sample to determine blood type. Likewise, the presence, absence, or amount of various CD antigen-bearing cells in a sample could be rapidly determined. In such examples, antibodies for each antigen of interest may be immobilized at discrete sensor locations in a sensor array. Cells expressing a corresponding antigen bind to the antibodies result in a change in resonant frequency at a particular sensor location. The following tables provides an exemplary list of CD and other antigens for use in such methods:

TABLE 1

| Exemplary CD antigens | | |
|---|---|---|
| Designation | Cells Expressing | Function |
| CD1 | Dendritic reticular cells, Langerhans cell histiocytosis, few lymphoblastic lymphomas | |
| CD2 | T cells, NK cells | LFA-3 (CD58) ligand |
| CD3 | T cells | T cell antigent receptor structure, signal transduction |
| CD4 | Helper T cells | MHC class II coreceptor, HIV receptor |

TABLE 1-continued

Exemplary CD antigens

| Designation | Cells Expressing | Function |
| --- | --- | --- |
| CD5 | T cells, B cell subset, CLL, mantle cell lymphoma | T cell activation, CD72 ligand |
| CD7 | T cells, NK cells, early myeloid cells, some AMLs | T and NK cell activation |
| CD8 | Cytotoxic and suppressor T cells, NK cells | MHC class I coreceptor |
| CD10 | Early B | Neutral endopeptidase |
| CD11b | Monocytes, granulocytes | Cell adhesion molecule, part of CD11/cd18 integrin |
| CD11c | Granulocytes, monocytes, hairy cell leukemia | Cell adhesion molecule, part of CD11/CD18 integrin |
| CD13 | Myeloid cells | Aminopeptidase N |
| CD14 | Monocytes | |
| CD15 | Granulocytes, Reed-Sternberg cells, edothelical cells | Lewisx antigen, cell adhesion and phagocytosis |
| CD16 | NK cells, granulocytes | Fc gamma RIII (IgG receptor) |
| CD19 | B cells | B cell activation |
| CD20 | B cells | Ca++ channel, B cell activation |
| CD22 | B cells | Cell adhesion molecule |
| CD23 | Activated B cells, CLL | Fc epsilon RII (IgE receptor) |
| CD25 | Activated T cells, activated B cells, hairy cell leukemia, ATL/L | Interleukin 2 receptor alpha chain |
| CD28 | T cells | Delivery of second signal during T cell activation, B7 (CD80/CD86) ligand |
| CD29 | Activated T cells | Cell adhesion molecule |
| CD30 | Activated T cell, Reed-Sternberg cells, anaplastic large cell lymphoma, germ cell tumors | Growth factor receptor (similar to TNF receptor) |
| CD33 | Myeloid cells | Sialic acid adhesion molecule |
| CD34 | Progenitor cells | |
| CD38 | Lymphoid progenitor cells, plasma cells | Leukocyte activation |
| CD40 | B cells | Growth factor receptor, B cell activation |
| CD41 | Megakaryocytes | gpIIb, cell adhesion molecule with CD61, fibrinogen/fibronectin receptor |
| CD42b | Megakaryocytes | gpIb, vWF receptor |
| CD43 | T cells, myeloid cells, some B cell lymphomas | |
| CD45 | Panhematopoietic | Signal transduction: tyrosine phosphatase |
| CD45RA | B cells, naïve T cells | Signal transduction: tyrosine phosphatase |
| CD45RO | Memory T cells | Signal transduction: tyrosine phosphatase |
| CD54 | Endothelium, activated cells | Cell adhesion molecule, receptor for CD11/CD18 integrin |
| CD55 | Most cells | Inhibits complement activation |
| CD56 | NK cells | Cell adhesion molecule |
| CD57 | NK cells | |
| CD59 | Many hematopoietic cells, decreased or absent in PNH | Blocks complement activity |
| CD61 | Megakaryocytes | bgIIIa, cell adhesion molecule with CD 41, fibrinogen receptor |
| CD62P | Activated platelets | Cell adhesion molecule |
| CD71 | Erythroid, lymphoid precursors | Transferrin receptor |
| CD80 | B cells, dendritic cells | T cell costimulatory molecule |
| CD86 | B cells, dendritic cells | T cell costimulatory molecule |
| CD95 | T cells | Transmits apoptosis signal (similar to TNF receptor) |
| CD103 | Intestinal epithelial lymphocytes | |
| CD122 | T cells | Interleukin 2 receptor beta chain |

TABLE 2

Other exemplary antigens of hematologic interest

| Antigen | Cells Expressing | Function |
| --- | --- | --- |
| HLA-DR | B cells, monocytes, myeloid progenitors, activated T cells | Class II MHC, antigen presentation |
| IgM heavy chain (mu) | Naïve B cells | Antigen recognition, B cell activation |
| IgG heavy chain (gamma) | Antigen-experienced B cells | Antigen recognition, B cell activation, humoral immunity |
| IgD heavy chain (gamma) | Naïve B cells | Antigen recognition, B cell activation |
| IgA heavy chain (alpha) | Antigen-experienced B cells | Antigen recognition, B cell activation, mucosal immunity |
| IgE heavy chain (epsilon) | Antigen-experienced B cells | Antigen recognition, B cell activation, hypersensitivity reactions |
| Kappa light chain | B cells | Antigen recognition, B cell activation |
| Lambda light chain | B cells | Antigen recognition, B cell activation |
| TdT | Immature lymphoid cells | Ig and TCR rearrangement |
| MiB-1/Ki-67 | Proliferating cells | |

In a similar manner, the array format can be applied to characterizing other cell populations, such as the species and/or serotype of bacteria in a sample or the binding characteristics of molecules displayed by phage or yeast display methods. In the latter case, antigens of interest may be immobilized at discrete sensor locations on a sensor array, and the ability of cells displaying the corresponding binding molecule bind to the antigen and result in a change in resonant frequency at a particular sensor location. A rank ordering of affinities of display molecules can be obtained by titrating the number of displaying cells applied to the sensor array.

Resonant sensors and sensor arrays also provide an attractive means to provide high throughput screening of molecules that bind to cell surface components such as receptors, or that compete with natural ligands for binding to these cell surface components. Conventional screening techniques typically yield hit rates in the 1-2% range on library sizes of 1-3 million compounds. Thus, for a "good" primary screen, something like 15,000 compounds will be identified as "hits". Secondary assays designed to eliminate compounds with adverse toxicity, adsorption, metabolic and elimination effects are applied together with elimination of compounds that bind irreversibly or non-specifically. The end result is still hundreds of compounds with specific binding properties, very few or in many cases, none of which will prove to have any clinical value. Such libraries of compounds can be used, together with acoustic resonant sensors, and particularly resonant sensor arrays, with advantageous increases in screening efficiencies. The use of various chemistries to protect, create hydrogels and/or attach compounds or polymers to the surface of a microfabricated mechanical resonance sensor are described above.

Using such sensors, surface chemistries, and signal processing, one or more arrays ($A_1 \ldots A_n$) may be created such that each arrayed sensor in a particular array comprises one or more immobilized molecular species from a library of interest. A population of cells, or cellular material (e.g., proteins, lipids, enzymes, receptors, etc.) may be contacted with this array, and binding of cells or cellular material to the sensors in the array may be determined. One or more "standard" sensors, e.g., comprising a molecular species having a known interaction for the cellular material of interest (e.g., a cell surface molecule present in the cell population), or comprising a molecular species known not to interact, may be included for normalization purposes.

Different arrays in an array "family" may comprise a defined set of properties, including, but not limited to: i) binding specificity, ii) binding affinity, iii) log P, iv) other properties indicative of structure/function relationships or v) combinations of these features. Subsequent arrays may be provided that exhibit a lesser, greater or simply different property or properties than the previous and/or following arrays. Using the data from screening each array in the "nested" family, and comparing that data to patterns from known targets, the researcher can quickly gain detailed insight into the identity and characteristics of the binding entity or entities. In addition, subsequent solution competition experiments with specific compounds on the array surfaces can be easily performed to yield rapid information about binding specificity and affinity.

Exemplary applications for such high-throughput screening method can include kinase target discovery, e.g., using a kinase nested family array. In these embodiments, arrays comprising known kinase inhibitors, $A(1) \ldots A(n)$ immobilized at or near a sensor membrane, such that material binding to the kinase inhibitors (e.g., cells, proteins, etc.) will be within the sensed volume of the sensor. are provided. All inhibitors on A(1), for example, may be non-specific and have binding affinities to known kinases characterized by a dissociation constant ($K_d$) in the range of $10^{-7}$ to $10^{-9}$. A second array may then be provided with inhibitors to known kinases having reduced binding affinities. Subsequent arrays may also be provided with different binding affinities or specificities to form the family of nested arrays. An expression product, cell population, tissue homogenate, or other target source may be contacted with A(1), and the binding pattern and affinities recorded. This procedure may be repeated with subsequent arrays in the array family. A pattern (hit signatures) may be obtained representing known kinases. Subsequently, array A(1) may be contacted with hits from A(2 ... n) to determine competitive displacement kinetics. In a similar manner, Nested Family Arrays can be used to quickly distinguish and characterize unknown proteases, esterases, nucleases and transferases.

In another example, orphan G-protein receptors may be identified using panels for comprising molecules known to interact with known G-protein receptors families can be prepared and used to screen cell preparations for possible orphan receptors. Such a panel would not only identify the presence and quantity of receptor in the cell expression mix, but also, by a resulting hit signature, assign a significant level of information about the nature of the receptor binding site and it's structural similarity to other receptors in the G-protein receptor families. In a like manner, other receptors, including nuclear hormone receptors, may be patterned and characterized.

Another relevant property of cells relates to their subcellular structure. Cells possess fibers which confer rigidity and the ability to exert forces on their environment. This includes but is not limited to intermediate filaments, microtubules, and contractile filaments such as actinomycin. In the case of contractile cells obtained from cardiac muscle, individual cells can exert forces on the order of 1 micronewton. If attached to the surface of a sensor, these forces would be capable of changing the stress in the membrane and hence the frequency of resonance. In addition to sensing the presence or absence of an attached cell by density, resonant sensors and sensor arrays may be used to sense physiologic differences in the strength of contraction (ionotropic changes) and in the rate (chronotropic changes) of muscle contraction.

Measurement of these changes are very important in the function of muscle, especially cardiac muscle, in which drugs are sought to affect these two properties for the management of angina or congestive heart failure. Thus, muscle cells cultured on a resonant sensor array substrate may be queried with one or more molecules, and the resulting effect on contraction determined. As stated above, the frequency of resonance of the resonant membrane is highly sensitive to stresses in the membrane. Changes in the force and rate of contraction of an adherent cell may be sensed by changes in the membrane resonance. In the spontaneously beating muscle cell, this will result in rhythmic modulation of the fundamental frequency at a much lower frequency. A high degree of resolution can be obtained in this spontaneously beating system because this low frequency signal can be easily distinguished from system noise. Inotropic changes will be seen as a greater degree of modulation where as chronotropic changes may be detected in the frequency rate of the modulation. The unperturbed frequency of resonance of the membrane is controlled by the method of deposition of the membrane, thickness and choice of materials. In the devices described herein, a very thin layer (0.3 micrometer) of material with high Young's modulus (silicon derivative) can be deposited under stress, to obtain a membrane with a membrane with a size and frequency range which minimizes damping by water. A 1 micronewton stress provided by the cell would be calculated to cause an 80 Hz change in frequency. This is well within the limits of resolution of the devices described herein. In addition, the effect of the cell on the frequency of resonance can be increased by decreasing the tension in the membrane. The high frequency of the device could be maintained by decreasing the diameter of the membrane, if necessary.

Once bound to a sensor array surface, either through specific interaction with affinity agents or by simple use of a sensor array surface as a cell culture substrate, immobilized cells can provide an ordered array for comparison of the biologic responses of various cell types. Specific attachment may be mediated by cell surface molecule(s), which may be bound to a receptor that exhibits a sufficient binding affinity for the cell surface molecule(s). The term "cell surface molecule" refers to a molecule, or a portion of a molecule, present on an external surface of a cell. Preferred cell surface components include, but are not limited to, receptors such as pIgR, a scavenger receptor, a gpi-linked protein, transferrin receptor, vitamin B12 receptor, FcRn, integrins selecting, cadherins, N-CAM, 1CAM, low density lipoprotein receptor; cargo carrier fragments such as pIgR stalk, members of the PGDF, FGF, and VEGF receptor families (e.g., Flt-1, Flk-1, Flt-4, FGFR1, FGFR2, FGFR3, FGFR4), and surface antigens. The length of time for attachment of the cell to the array may be limited by capping and shedding or endocytosis of integral membrane proteins; however, such limitations can be overcome by a number of procedures. For example, assays could be completed quickly, e.g., preferably within 2 hours of immobilization; more preferably within 1 hour; and even more preferably within 30 minutes, thus limiting turnover of membrane components. Alternatively, assays could be performed in under conditions which slow or prevent membrane movement and/or turnover (e.g. at reduced temperatures or in the presence of endocytosis inhibiting agents such as EDTA). Another and preferred approach would be to provide additional sites for the cell to anchor to the sensor, such as by mixing an integrin or other protein comprising an RGD containing peptide with an antibody for a cell surface component. In this case, initial rapid immune mediated attachment would be followed by gradual spreading and attachment via integrins. The attached cells could then be treated with a variety of chemical or biologic agents, and their response monitored.

A resonant sensor array comprising cells of interest may be used, for example, to determine the chemosensitivity and specificity of chemotherapeutic agents. In such an embodiment, an array of leukocytes obtained from a patient of interest may be immobilized by a panel of CD specific antibodies. The panel would then be treated with increasing doses of individual chemotherapeutic agents. The specific response of the leukemic cells could be measured by its selective detachment from the array, indicating selective injury or death to this cell type, and thus predicting toxicity (or lack thereof) in cells other than the target cells. In similar fashion, the addition of a biologic agent to a resonant sensor array comprising cells of interest may be used to determine therapeutic specificity. Examples of this would be the testing of the specificity and toxicity of therapeutic monoclonal antibodies, aptamers, antisense, ribozymes or interfering RNAs.

Such a resonant sensor array comprising cells of interest may also be used to measure the susceptibility of related cells to viral, bacterial, or parasite infection. Such infection would result in changes in the physical properties of the cell (size, density, rigidity or cell death) which would be detected by the sensor.

Another example for the use of resonant sensor arrays comprising cells of interest is the addition of biologic agents to further characterize a cell by the addition of specific immunologic reagents. This could be used for subset determination (e.g. through the use of another CD specific antibody to look at doubly positive cells), or to look at activation state of the cell (e.g. to look at cytokine or chemokine receptor activation on the surface). Toxicity or apoptosis (e.g. using annexin V plus actinomycin-7AAD antibodies), endocytic or phagocytic activity (e.g., opson coated beads) could also be tested. In each of these cases, additional sensitivity could be obtained by coupling a mass enhancement moiety to these secondary immunoreagents as discussed above.

In still another example, the ability of chemical or biologic agents to modify the number and or affinity of cell surface receptors on arrayed cells may be determined. For example, cells may be immobilized to the array by binding to immobilized peptides with known affinity toward the receptor. Addition of an agent which altered normal recycling of the receptor, or affinity of the receptor (e.g., via phosphorylation and/or receptor dimerization) may result in displacement of the cell from the array surface. This is particularly useful, for example, in the case of the opioid receptor, where some opioid mimetics selectively modulate receptor turnover. Differences in these properties may contribute to development of tolerance and addiction.

The skilled artisan will recognize that a commonly used refinement of the approaches discussed above is to create subregions within a particular resonant sensor array which allow small groups of sensors to be exposed to different chemical or biochemical reagents. As discussed in detail above, such a refinement facilitates more efficient and higher throughput screening of compounds for a variety of purposes. Molecules characterized according to their ability to bind at the resonant sensors may be further characterized by recovery and further analysis, e.g., by mass spectroscopy, electrophoresis, microsequencing, NMR spectroscopy, etc. Additional advantages gained from the use of resonant sensors and sensor arrays include the following:

Uses no molecular labels. Sensor surfaces in this invention are responsive to mass binding. Immobilizing probe compounds, with known binding affinities to specific target families creates the ability to pattern unknown targets, without labels that may affect the target's binding properties. As the sensor signal requires no fluorescent, isotopic or labels of any kind in preferred embodiments, the sample can be presented to the sensor in native form.

Allows use of complex biological mixtures. Conventional assays for biological activity require that one or more binding partners be purified and subsequently labeled with a molecular reporter capable of being detected at relevant biological concentrations. As this sensor is label-free, no purification may be required. The sensor surface detects binding only as determined by the biological specificity imparted by the probe molecule. Thus, complex mixtures or even crude cell suspensions can be presented to the surface without purification or sample pre-treatment of any kind. In addition to greatly simplifying and streamlining the assay process, this capability allows fundamentally new information to be generated, as many protein targets cannot be purified.

Allows use of very small volumes. The sensor surface is very small (approximately 40 u) as is the array size ($<1$ cm$^2$), requiring very little sample volume for a complete analysis. Our models indicate that a complete sample analysis will require less than 20 µl of total sample volume. This is a several thousand fold reduction over the best of currently used techniques. Increased dynamic range by deep query and use of a hydrogel also leads to decreased crowding of ligands and hence less steric hinderance.

EXAMPLES

The following examples serve to illustrate the present invention. These examples are in no way intended to limit the scope of the invention.

Example 1

Use of a Resonant Sensor as a Density Sensor

As described above, the device detects changes in density conferred by concentration of biological molecules in the space above the sensor. Biological molecules such as protein (density 1.3) DNA (density 1.5) and RNA (density 1.7) are substantially higher than that of water (density 1.0). and substantially higher than those of cells (density 1.05-1.09). However, when present in a monolayer, this altered density is barely seen because it only creates a very thin layer of altered density and the net density in the sphere is not substantially changed. The sensitivity of detection of the devices described herein may be amplified by creating a 3 dimensional region of binding (using a hydrogel) which extends farther out into the hemisphere of water interrogated by the resonant membrane. The hydrogel-bonded resonant sensor is prepared as described in U.S. patent application Ser. No. 10/306,506 (filed Nov. 26, 2002).

An alternative approach to increase sensitivity is to couple secondary labeling reagents agents to a mass enhancement moiety, such as gold beads, as was described above. As a first example, gold or magnetic beads are conjugated to one of 3 reagents: Anti-IgG, Anti-IgM or Anti-IgE. A small sample of a patient's serum is mixed separately with each of these three, bead bound reagents. This Ig-class-specific immunoaffinity reagent may be purified directly out of whole blood or serum merely by centrifugation or application of an external magnet. This can form the basis for a greatly simplified protocol for sample preparation. These bead-antibody complexes may then be applied directly to the array. Sequential passage of IgE, IgM and IgG reagents across an array of common allergic and infectious antigens could be used to characterize the allergic potential and immune status of a patient. This approach could also be used to collect and quantify rare or secreted products.

Example 2

Use of a Resonant Sensor to Map Expression of Proteins

Antibodies immobilized to the resonant sensor may be used to map the expression of cellular proteins, much as nucleic acid "chips" currently are used to map the expression of cellular RNAs. In this case, an unlabeled protein extract is applied to a resonant sensor array containing antibodies of interest embedded into a hydrogel. The hydrogel-bonded resonant sensor is prepared as described in U.S. patent application Ser. No. 10/306,506 (filed Nov. 26, 2002). These antibodies may detect all forms of the protein, or may be designed to detect specific conformers (e.g. phosphorylated forms). Binding of the protein confers a density shift, which may then be augmented by addition of a mass enhancement reagent. This reagent could be used to distinguish conformational subtypes (e.g. a phosphorylated form as above) or may be a natural dimerization partner. Thus allowing determinations of both structure (total amount of specific protein) as well as function (ability to interact with other proteins). Changes in mass or density within the sensed volume above each sensor in the array are monitored by monitoring resonant frequency of the sensor membrane.

Example 3

Use of a Resonant Sensor to Assess Enzyme Activities

An array of enzyme substrates is produced by embedding the substrates in a hydrogel. The hydrogel-bonded resonant sensor is prepared as described in U.S. patent application Ser. No. 10/306,506 (filed Nov. 26, 2002). The resulting array is contacted with one or more enzymes of interest (e.g., kinases, hydrolases, esterases, etc.) and the resulting modification to each substrate is detected by a mass conferring specificity agent (e.g. a phosphor-tyrosine specific antibody or a phosphor specific chelate. Changes in mass or density within the sensed volume above each sensor in the array are monitored by monitoring resonant frequency of the sensor membrane.

An enzymatic activity sensor as described is used to detect changes in mass conferred by enzymatic addition of mass to a substrate. In the case of DNA assays, the rolling circle, anchored SDA, anchored PCR and anchored NASBA reactions may be monitored by such a sensor. In these cases, presence of a DNA species in solution is captured by specific hybridization to a enzymatic activity sensor, where the enzyme substrate immobilized at each sensor location is an oligonucleotide target. Amplification of nucleic acid sequences leads to the covalent accumulation of considerable mass on the surface of the resonant sensor.

Example 4

Use of a Resonant Sensor to Assess Transcription Factor Activation

A resonant sensor array comprising mixed affinity reagents such as nucleic acid transcription factor targets and antibodies to one or more transcription factors is produced as described herein. Binding to antibodies would determine the total amount of transcription factor present and the amount and type of dimer partners available. Binding to DNA targets, would indicate the amount of functional protein present (e.g. phosphorylated transcription factor) as well as the dimer partner chosen. Changes in mass or density within the sensed volume above each sensor in the array are monitored by monitoring resonant frequency of the sensor membrane.

Thus, the present invention provides a sensor assembly and sensors with improved performance through a thermally insensitive environment and short pathways for signals to travel to processing components. Further, the modular construction for the sensors and housing modules allows replacement of the sensors at a lower cost. Detection and analysis of the signals from the sensors is greatly improved through the use of the disclosed embodiments.

While preferred embodiments and methods have been shown and described, it will be apparent to one of ordinary skill in the art that numerous alterations may be made without departing from the spirit or scope of the invention. Therefore, the invention is not limited except in accordance with the following claims.

We claim:

1. A method of forming a sensor assembly, comprising:
 1) forming a housing assembly;
 2) accommodating a sensor module in the housing assembly further comprising:
  a) fabricating a membrane layer of a sensor on a top surface of a substrate, the substrate comprising a plurality of sensing regions, the membrane layer having an electrode within or below the top surface;
  b) forming a plurality of cavities corresponding to each said sensing region;
  c) forming a second electrode of the sensor at a bottom of each said cavity; and
  d) providing a plurality of conductive vias from each said cavity to a bottom surface of the substrate, the bottom surface being opposite the top surface; and
 3) forming a fluidics module over the sensor module, comprising:
  a) attaching a nonconductive frame to the substrate to form a fluid sample reservoir over the top surface of the substrate.

2. The method of claim 1 wherein forming a fluidics module over the sensor module further comprises:
 b) forming a fluidics base;
 c) forming a window assembly by engaging a frame with the fluidics base; and
 d) positioning a window directly above the fluid sample reservoir.

3. The method of claim 1 further comprising evacuating and sealing each said cavity.

4. The method of claim 1 further comprising providing a fluid sample to the fluid sample reservoir over the membrane layer.

5. The method of claim 1 further comprising:
 a) mounting an electronic component in the housing assembly; and
 b) providing an electrical connection between the sensor module and the electronic component.

6. The method of claim 5 further comprising providing the electrical connection by electrically engaging contacts of the electrical component with the conductive vias.

7. The method of claim 1 further comprising directing a fluid to the reservoir.

* * * * *